(12) United States Patent
Turley

(10) Patent No.: US 10,131,717 B2
(45) Date of Patent: Nov. 20, 2018

(54) TOPICALLY ADMINISTERED, SKIN-PENETRATING GLYCOSAMINOGLYCAN FORMULATIONS SUITABLE FOR USE IN COSMETIC AND PHARMACEUTICAL APPLICATIONS

(71) Applicant: London Health Sciences Centre Research Inc., London (CA)

(72) Inventor: Eva Turley, London (CA)

(73) Assignee: LONDON HEALTH SCIENCES CENTRE RESEARCH INC., London (CA)

( * ) Notice: Subject to any disclaimer, the term of this patent is extended or adjusted under 35 U.S.C. 154(b) by 0 days.

(21) Appl. No.: 14/727,257

(22) Filed: Jun. 1, 2015

(65) Prior Publication Data
US 2015/0368373 A1    Dec. 24, 2015

Related U.S. Application Data

(63) Continuation of application No. 13/696,887, filed as application No. PCT/CA2011/000512 on May 4, 2011, now abandoned.

(30) Foreign Application Priority Data

May 10, 2010 (CA) ..................... 2703532

(51) Int. Cl.
| | | |
|---|---|---|
| *C08B 37/08* | (2006.01) | |
| *A61K 8/73* | (2006.01) | |
| *A61K 9/00* | (2006.01) | |
| *A61K 9/06* | (2006.01) | |
| *A61Q 19/08* | (2006.01) | |
| *A61K 8/64* | (2006.01) | |
| *A61K 8/65* | (2006.01) | |
| *A61K 8/66* | (2006.01) | |
| *A61K 38/17* | (2006.01) | |
| *A61K 38/39* | (2006.01) | |
| *A61K 38/45* | (2006.01) | |
| *A61K 38/48* | (2006.01) | |
| *A61K 47/36* | (2006.01) | |
| *A61Q 19/00* | (2006.01) | |
| *A61K 47/54* | (2017.01) | |

(52) U.S. Cl.
CPC ............ *C08B 37/0072* (2013.01); *A61K 8/64* (2013.01); *A61K 8/65* (2013.01); *A61K 8/66* (2013.01); *A61K 8/735* (2013.01); *A61K 9/0014* (2013.01); *A61K 9/06* (2013.01); *A61K 38/17* (2013.01); *A61K 38/39* (2013.01); *A61K 38/45* (2013.01); *A61K 38/4893* (2013.01); *A61K 47/36* (2013.01); *A61K 47/544* (2017.08); *A61Q 19/007* (2013.01); *A61Q 19/08* (2013.01); *C12Y 204/01212* (2013.01); *C12Y 304/24069* (2013.01)

(58) Field of Classification Search
CPC ........ A61K 38/15; A61K 9/0019; A61K 9/19; A61K 47/10; A61K 47/26; A61K 9/06; A61K 38/39; A61K 47/36; A61K 47/48053; A61K 19/007; A61K 8/65; C08B 37/00; C08B 37/0072; A61Q 19/08; C12Y 304/24069
See application file for complete search history.

(56) References Cited

U.S. PATENT DOCUMENTS

| | | | | |
|---|---|---|---|---|
| 7,393,938 B2 * | 7/2008 | Yedgar | ............... | A61K 47/4823 536/18.7 |
| 7,504,384 B2 * | 3/2009 | Yedgar | ................. | A61K 31/727 514/42 |
| 2003/0113349 A1 * | 6/2003 | Coleman, III | ....... | A61K 9/0014 424/239.1 |
| 2004/0241248 A1 * | 12/2004 | Margalit | .............. | A61K 9/0043 424/493 |
| 2008/0248092 A1 * | 10/2008 | Margalit | .............. | A61K 9/1271 424/450 |
| 2011/0008422 A1 * | 1/2011 | Dekel | .................. | A61K 9/1271 424/450 |

OTHER PUBLICATIONS

Brown et al., Absorption of Hyaluronan Applied to the Surface of Intact Skin, J Invest Dermatol 113:740-746, 1999.*
3 pages from https://en.wikipedia.org/wiki/Critical_micelle_concentration directed to Critical Micelle Concentration, 2017.*

* cited by examiner

*Primary Examiner* — Kartheinz R. Skowronek
*Assistant Examiner* — Joseph Fischer
(74) *Attorney, Agent, or Firm* — Eduardo Krupnik

(57) ABSTRACT

The present invention relates to topical glycosaminoglycan compositions, particularly hyaluronan compositions, that facilitate the penetration of modified glycosaminoglycans through the skin barrier into the epidermal and dermal layers of the skin, thereby allowing for the dermal administration of a glycosaminoglycan, such as hyaluronan, without requiring an injection. Through their ability to deliver hyaluronan to the epidermal and dermal layers, the present formulations are therefore suitable for use in dermal rejuvenation, enhancement, hyaluronan replenishment and protection therapy. The glycosaminoglycan compositions are also useful as delivery devices to facilitate the dermal and transdermal delivery of cosmetically and pharmaceutically active substances, including pharmaceuticals, polypeptides, proteins and similarly sized biomacromolecules, through the skin barrier.

39 Claims, 17 Drawing Sheets

Figure 2:
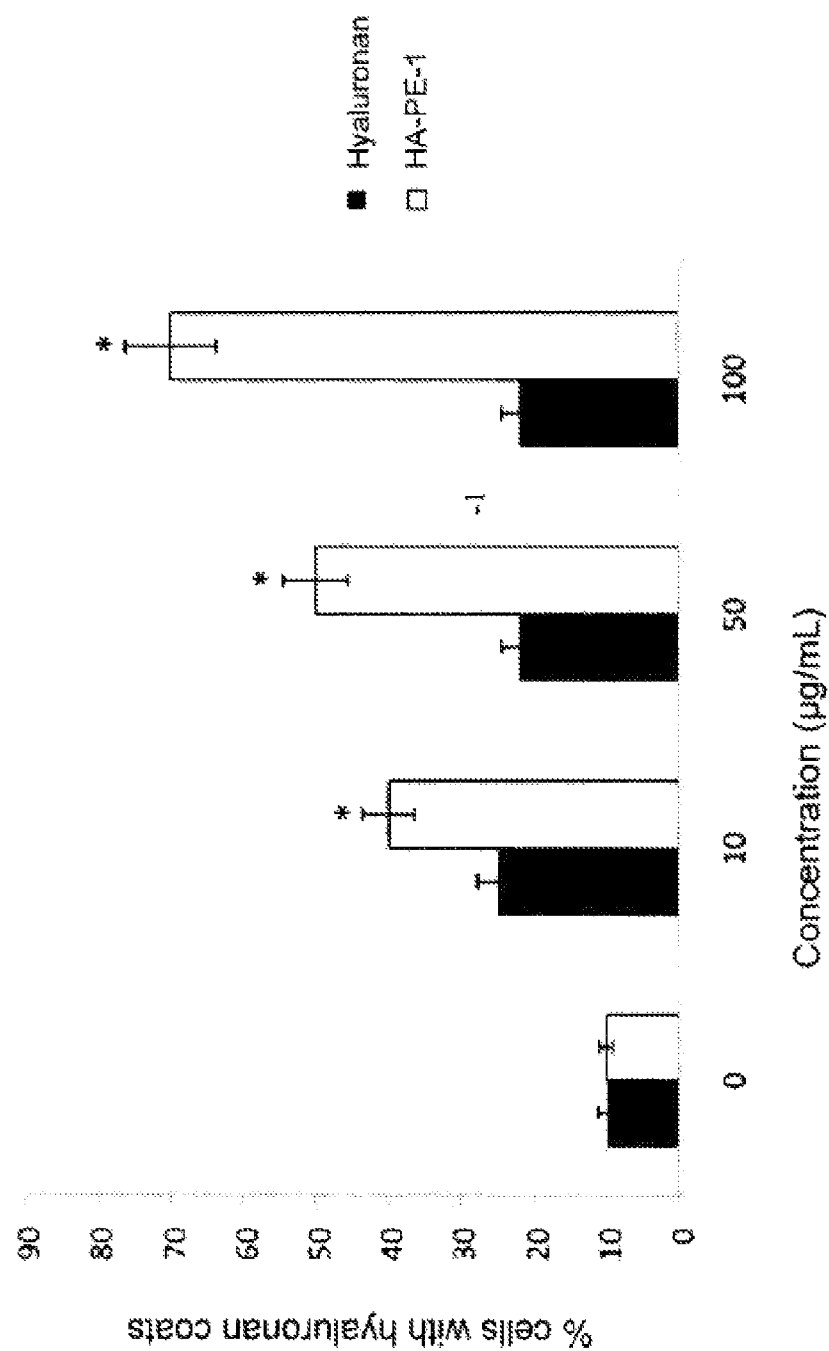

Figure 1
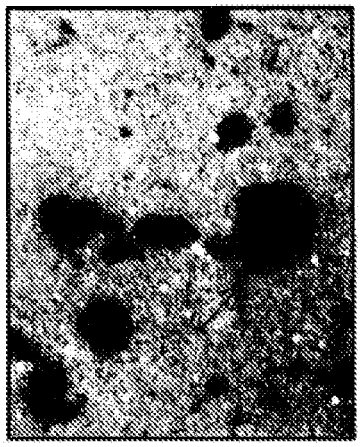
Image 12 (HA-PE-1)
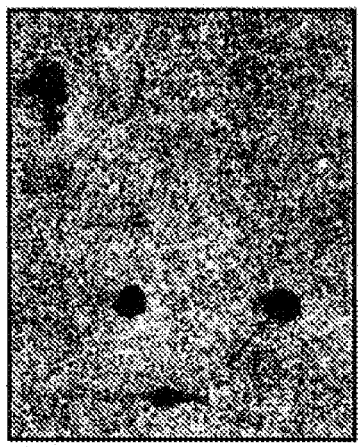
Image 12 (hyaluronan)
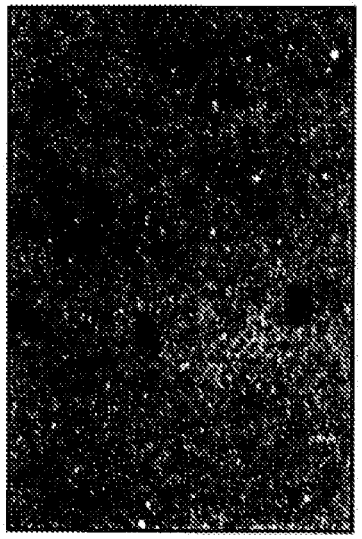
Image 11 (control)

Figure 6
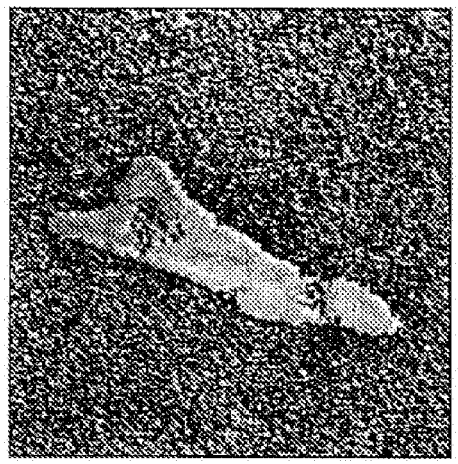
Image 63
(SKL catalase and HA-PE-1)
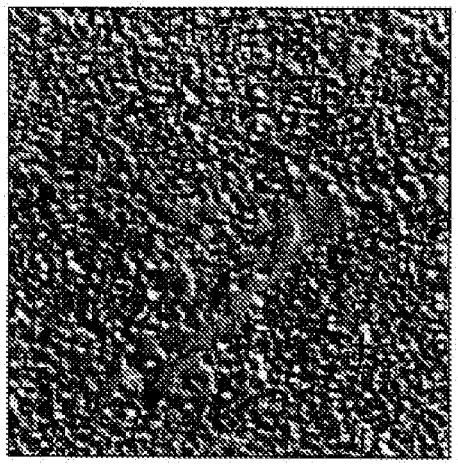
Image 62
(HA-PE-1)
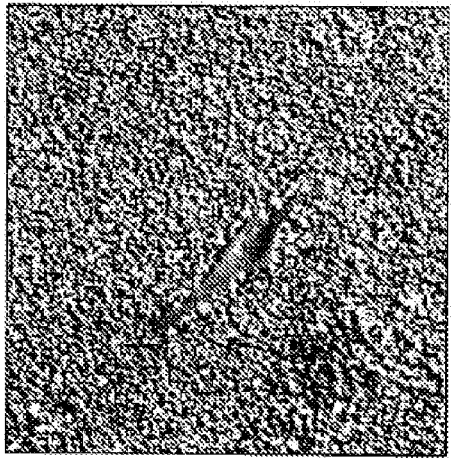
Image 61
(SKL catalase)

Figure 11
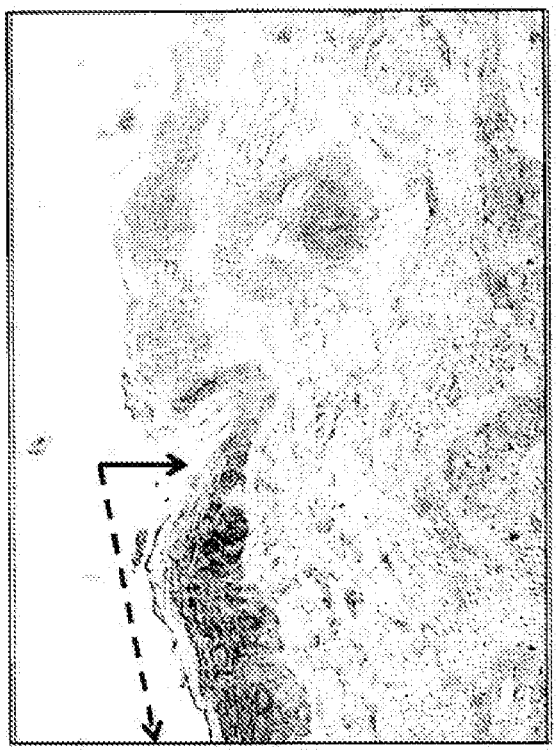
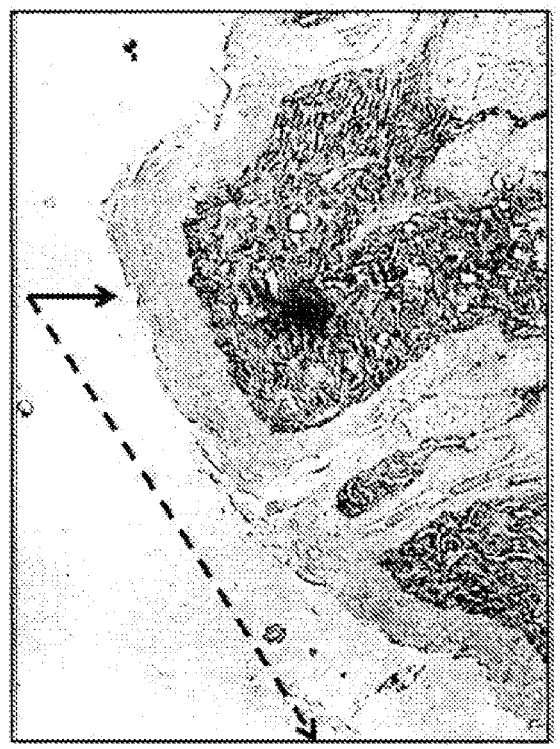

Figure 13
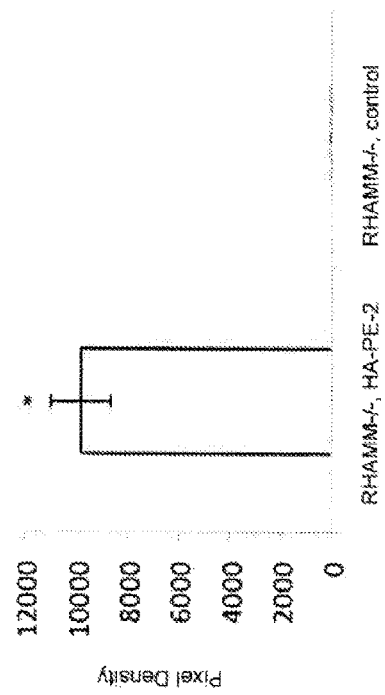
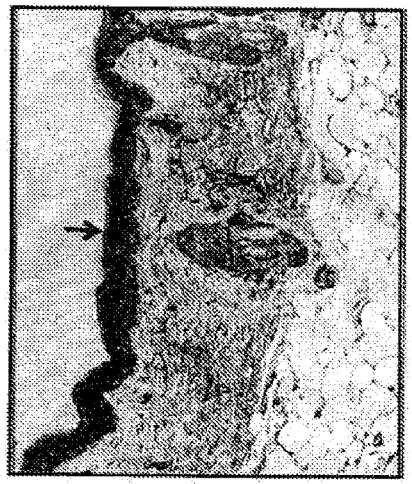
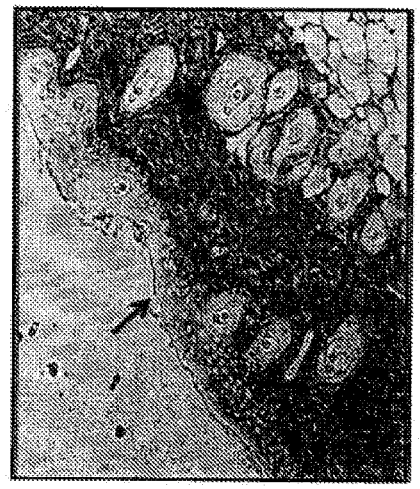

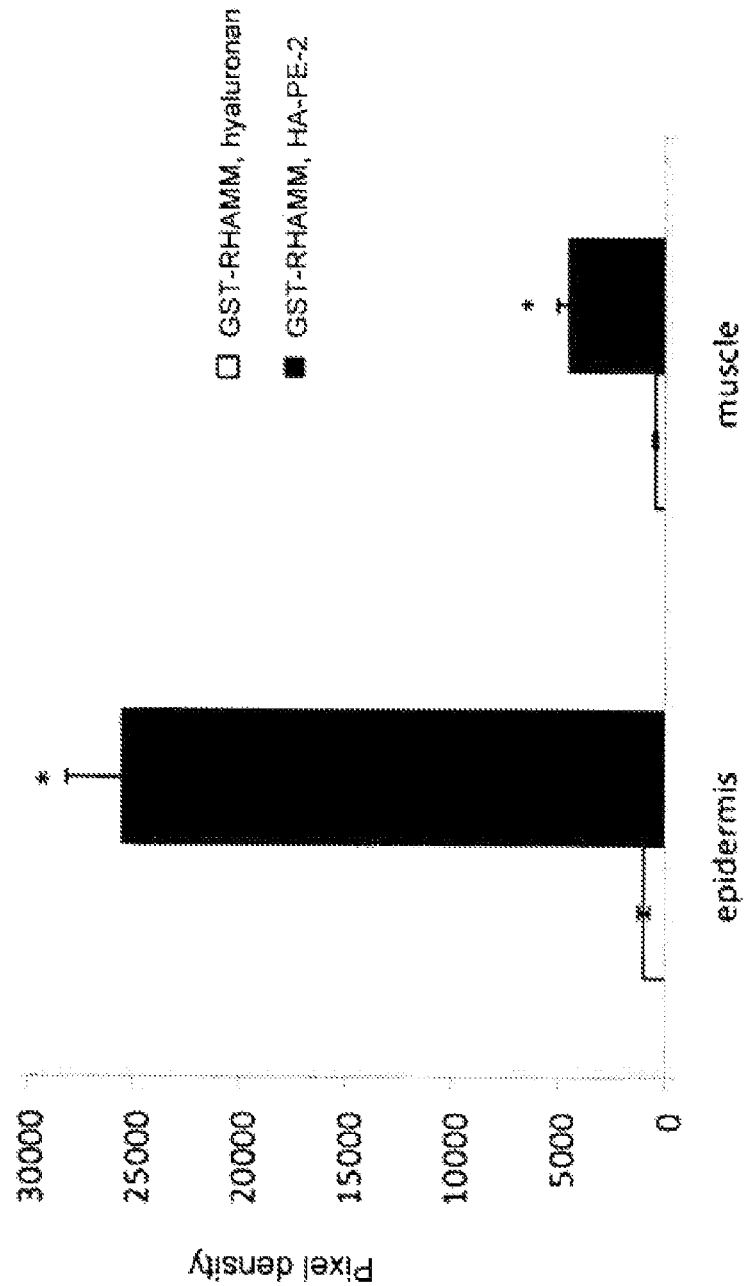

TOPICALLY ADMINISTERED, SKIN-PENETRATING GLYCOSAMINOGLYCAN FORMULATIONS SUITABLE FOR USE IN COSMETIC AND PHARMACEUTICAL APPLICATIONS

CROSS REFERENCE TO RELATED APPLICATIONS

This application is a continuation of U.S. patent application Ser. No. 13/696,887 filed Nov. 8, 2012, which in turn is a national stage application under 35 U.S.C. 371 of International Application No. PCT/CA2011/000512, filed May 4, 2011, which in turn claims the benefit under 35 U.S.C. 119(e) of Canadian Patent Application No. 2,703,532, filed May 10, 2010, the contents of each of which are hereby incorporated by reference into the present disclosure.

FIELD OF THE INVENTION

The present invention relates to topical glycosaminoglycan formulations that facilitate the penetration of glycosaminoglycans modified through the covalent linkage of lipid moieties to 1 to 10% of the disaccharide monomer units through the skin barrier into the epidermal and dermal layers of the skin, thereby allowing for the dermal administration of the glycosaminoglycan without requiring an injection. In particular, through their ability to deliver hyaluronan to the epidermal and dermal layers, which is retained in the skin for greater periods of time than topically delivered hyaluronan, the present formulations are therefore suitable for use in dermal rejuvenation, enhancement, hyaluronan replenishment, and protection therapy. The compositions may also be used as delivery devices for therapeutic compounds, including polypeptides, proteins and other similarly sized biomacromolecules, facilitating their passage through the skin barrier. Also provided is a method of manufacture for the compositions wherein the degree of covalent linkage of the lipid moiety to the glycosaminoglycan is controlled by the use of an activating agent as the limiting reagent.

BACKGROUND OF THE INVENTION

The process of facial aging occurs in a series of predictable events manifesting in the loss of both skin volume and elastic tone. Volume loss in skin, which results from many factors, including collagen breakdown, leads to the atrophy of subcutaneous fat, underlying muscle and fasciae layers of the skin, contributes to nasolabial folds, the loss of definition of the jaw line and the coarsening of skin. Loss of elastic tone in the skin results in flaccid, sagging facial tissue. To counter these effects, rejuvenation procedures attempt to correct both volume loss and tissue tone to result in the natural appearance of treated skin. These procedures may involve the use of tissue fillers, e.g., collagen injections, or the tightening provided by "lift" surgery, among other options, used individually or in combination.

A number of temporary tissue fillers, such as collagen, hyaluronan and hydroxyapatite are currently available, however, these fillers are administered through a series of injections, and provide only a temporary effect, often failing to extend beyond 12 months in the case of collagen and hyaluronan. Longer term solutions, such as hydroxyapatites (which can last 2-5 years), also include fat autografting (lasting 1 to 3 years), which uses subcutaneous adipocytes, to correct both facial volume loss and sagging to restore a more youthful appearance to facial skin.[1,2,3] The after effects of injection treatments, which can last up to one week, can include swelling, redness, pain, bruising, and tenderness. Additionally, the treatments require skilled application through multiple injections, and carry a risk of infection at injection sites.

Keratinocytes are perhaps the most important cell type in providing a youthful appearance for skin. Thus, they are necessary for maintaining skin hydration and are particularly susceptible to the aging effects of environmental factors such as UV radiation since they are more constantly exposed to these factors than other skin cell types. Furthermore, recent evidence suggests that genetically determined keratinocyte factors may also contribute to the intrinsic aging process. Since keratinocytes produce paracrine factors that affect the health/functioning of fibroblasts and other dermal cells, factors that are detrimental to keratinocyte functions are therefore also detrimental to dermal cell functions.[6]

Hyaluronan (also known as hyaluronate and hyaluronic acid) is a large, negatively charged glycosaminoglycan polysaccharide that is ubiquitous in the body and is present in particularly large amounts in the skin.[4] Both the dermal and epidermal skin layers are rich in hyaluronan, which is present as part of the encased extracellular matrix (which also contains collagen and other proteins), where it surrounds the cells (e.g., epidermal keratinocytes and dermal fibroblasts).[5] Although young skin is rich in pericellular hyaluronan in both keratinocyte and dermal layers, the amounts are reduced in both layers of aging skin, with the loss of hyaluronan from the keratinocyte layer being much more marked than in the dermal layer.[6]

In youthful skin, hyaluronan efficiently encases keratinocytes in the epidermis and fibroblasts in the dermis in a jelly like capsule (the cell coat), which provides cells with adequate growth and nutrient factors that promote the collagen and elastin production typical of youthful appearing skin. In addition to hyaluronan, the primary component of the cell capsules or coats, are also found extracellular proteins and other matter, such as collagens, proteoglycans (PG) such as TSG-6, and other glycosaminoglycans. The 3-dimensional structure of hyaluronan is of a shallow helix (with high molecular weight forms being detectable as long linear chains) that can tangle on itself, thereby providing an ideal template for assembling matrices around cells. These capsules or encasements are generally retained around cells through the binding of hyaluronan to cellular receptors, e.g., CD44, RHAMM, LYVE 1, and others. As skin ages, the ability of dermal fibroblasts and keratinocytes to maintain their hyaluronan capsules diminishes, resulting in the dehydrated and sagging appearance of aging skin.[5,7] Additionally, when skin is traumatized, e.g., through exposure to excessive UV radiation (sunburned), hyaluronan production by cells in the dermis is decreased, leading to an increase in hyaluronan degradation and the increased presence of hyaluronan degradation products in the skin.

Capsules of hyaluronan contain both structural matrix proteins that hydrate and protect cells, as well as nutrients, cytokines, hormones, and growth factors that are necessary for sustaining the optimal metabolic and differentiation status of cells. The ability to provide building matrices is a major factor underlying the use of hyaluronan to promote youthful skin. A second factor is the visco-elastic properties of hyaluronan, which affects the diffusion of nutrients from the vascular supply and the elasticity of skin; collectively these effects provide the texture and smoothness typical of youthful skin. A third factor is the ability of pericellular hyaluronan to provide a target for reactive oxygen species (ROS), which may be produced after exposure to UVA/B radiation, that can attack and fragment hyaluronan, in turn protecting other cellular factors from ROS-induced damage. A final factor is related to the direct biological effects of hyaluronan on keratinocyte and fibroblasts. Hyaluronan promotes both the proliferation and differentiation of keratinocytes. For example, factors such as retinoic acid, which enhance keratinocyte differentiation, also increases the pericellular hyaluronan coat. Furthermore, hyaluronan added to keratinocytes in vitro or in vivo promotes the thickness of the keratinocyte layer and enhances keratinocyte differentiation as detected by CD44 and keratin expression.[5] Hyaluronan also affects fibroblast differentiation by blocking trans-differentiation into myofibroblasts, which are dermal cells that produce high levels of collagen I and have intrinsic contractile properties, both of which promote wrinkle formation.

Over time, cellular hyaluronan coats are degraded (fragmented) and are increasingly taken up by cells as part of the aging process. This degradation is due in part to the build up of oxygen free radicals that occurs over time, and to changing genetically regulated developmental program (e.g., aging) that promote the release of hyaluronidases, which break down or fragment the hyaluronan coat. The resulting fragments stimulate the uptake machinery of the cell leading to disassembly and destruction of the hyaluronan coat by cellular lysozymes. In addition to being increasingly depleted from aging skin, particularly from around keratinocytes, it has also been found that hyaluronan is depleted from areas of wrinkled skin in youth resulting from exposure to UVA/UVB radiation, steroid use or inflammation.[5,6,8,9]

Hyaluronan receptor CD44 is constitutively expressed on keratinocytes and other cells in the skin, and is believed to be essential for the retention of hyaluronan around cells in layers known as "cell coats", and for appropriate hyaluronan metabolism in the skin.[5,10,11,12] The CD44 receptor is lost from skin during the aging process and following exposure to aging factors such as UV radiation or diseases/factors that cause skin atrophy.[5,9] In contrast, RHAMM, a further hyaluronan receptor, that is normally not highly expressed in normal skin, has its expression is increased with exposure to UVA/B and other injuring factors. RHAMM is thought to promote the ability of CD44 to internalize/metabolize hyaluronan. Non-integral, extracellular hyaluronan binding proteins such as TSG-6, are also important in the production and retention of hyaluronan cell coats surrounding dermal cells.[13]

Although hyaluronan is known to have ideal properties for use as a tissue filler in re-capturing the properties of youthful skin, the only currently available products producing their effect beneath the skin barrier rather than upon the surface of the skin, are cross-linked forms of hyaluronan that are injected to smooth facial wrinkles and to increase the volume of facial areas, such as the lips. While cross-linking of hyaluronan does enhance its retention at the injection site, these injections are not permanent and must be repeated on a regular (6-12 months) basis if the rejuvenating effect is to be preserved. However, the cross-linking of hyaluronan with itself is believed to reduce its ability to bind to cell-surface receptor proteins, a key property necessary for the encasement of cells by coats of hyaluronan. A further difficulty encountered include the difficulty to localize or "smooth" injected hyaluronan evenly under the skin. Thus, while the use of injectable hyaluronan may act as an effective temporary filler, it is not able to act in the same manner as natural hyaluronan to provide a cell-coating effect. While degradation of cross-linked injectable hyaluronan fillers could conceivably serve as a source of hyaluronan, retention of the hyaluronan is not expected owing to the known depletion of hyaluronan receptors on dermal cell surfaces and the high rate of hyaluronan degradation within the skin.

Since injectable fillers containing cross-linked hyaluronan are only administered at the site of the wrinkle or nasolabial fold, these treatments do not serve to "rejuvenate" the skin by replenishing the depleted hyaluronan levels in adjacent areas; rather, injectable treatments provide an appearance of rejuvenation by filling the depressed area. As a result, treatment with injectable dermal fillers do not aid in preventing or delaying the appearance of new wrinkles in adjacent, untreated areas, nor do they address the underlying issues of hyaluronan deficiency, and the consequent decreases in skin hydration.

Owing to its natural presence in skin, and its depletion during aging, exposure to UV radiation (sunburns and photoaging), and other skin trauma, hyaluronan is also included in many skin products in addition to its use as an injectable filler. Topically applied hyaluronan must gain entry through the hydrophobic layer of ceramide/keratin covering the outer layers of keratinocytes. However, since hyaluronan is a polyanion, it is not expected efficiently to cross the skin's keratinocyte layer. Therefore, topical hyaluronan either remains a surface treatment (e.g., traditional hyaluronan-containing skin creams) or must be injected if significant penetration into the skin is desired (e.g., in the treatment of wrinkles where cross-linked hyaluronan is injected).

It has been reported in the art that certain molecular weights of hyaluronan are able to pass through the skin barrier to some degree. Brown et al.[14] indicate that hyaluronan with molecular weights of 250 and 400 kDa, formulated with the known penetration enhancers polyethylene glycol and benzyl alcohol, passes through the skin barrier. While some other reports have indicated that undefined fractions reported to contain 40-400 kDa hyaluronan can pass through mouse and human skin,[5] it has also been indicated that >400 kDa native hyaluronan does not cross the skin when applied topically.[5,15] Furthermore, while Brown et al. were able to demonstrate that hyaluronan was able to pass through the skin barrier, it was also clear that the proportion of hyaluronan penetrating the skin was low and that the hyaluronan rapidly passed into the bloodstream and also exhibited rapid degradation. Kaya et al.,[5] have also demonstrated that topically applied hyaluronan was poorly retained in the epidermal layer, retention was transient in the dermal layer and applied hyaluronan was taken up by dermal cells and keratinocytes. Therefore, merely enabling the passage of hyaluronan through the skin barrier will not necessarily provide a useful effect; for many uses it may also be necessary for the hyaluronan to have a prolonged residence time in order to observe an effect. This is highlighted by the use of transdermal carriers to deliver hyaluronan through topical administration by Schultz et al. (U.S. Pat. No. 4,808,576). Although such applications are successful in facilitating the passage of hyaluronan through the skin barrier, the hyaluronan is not retained within the skin but instead continues to pass to the underlying joints and tendons. In addition, the requirement for a transdermal carrier, the most effective of which is DMSO, is generally not compatible with prolonged use.

Schwach-Abdellaoui and Malle (WO 2008/000260) describe compositions possessing moisturizing and anti-wrinkle properties comprising hyaluronan of two molecular weight fractions. A first, low molecular weight fraction (50 kDa), is stated to be able to pass through the skin barrier, whereas the second, higher molecular weight fraction (300 kDa) is stated to provide its more pronounced effect in diminishing skin roughness by accumulating preferentially at the surface of the skin. This use of hyaluronan, which is typical in cosmetic preparations, relies upon the use of hyaluronan as a short-lived external filler that, owing to the water soluble nature of hyaluronan is removed when the face is washed. As noted with regard to Brown et al., the proportion of hyaluronan able to pass through the skin barrier is low, and that which is able to pass through the skin barrier has a low retention rate within the skin itself. As a result, rather than relying upon topically applied hyaluronan, current biorejuvenation procedures, such as mesotherapy,[16] utilize injected, non-crosslinked, hyaluronan, either alone or with other active ingredients.

Thus, there remains a need in the art to develop methods of delivering higher molecular weight fractions of hyaluronan through the skin barrier without requiring injections. Higher molecular weight hyaluronan fractions (e.g., >100 kDa) are expected to be more bioresilient and to be better able to mimic the higher molecular weight hyaluronan naturally found in the skin.

Hyaluronan fragments have recently been shown to have therapeutic effects on wound repair and physiology of normal skin. Although these fragments penetrate skin better than higher molecular weight hyaluronan, they are not retained in the extracellular compartments of skin.[5]

To date, there have been a number of examples of hyaluronan, and other glycosaminoglycans, being modified through the linking of lipids for a variety of purposes. Sakurai et al. (U.S. Pat. No. 5,464,942) describes the preparation of lipidated glycosaminoglycans (including hyaluronan) where a single lipid side chain is added to either a terminal position or a single random internal position of a glycosaminoglycan. These compositions are stated to be able to inhibit the adhesion of cancer cells to blood vessel endothelial cells and their extracellular matrices.

Yerushalmi et al. (WO 2006/050246) describes the preparation of particulate lipidated glycosaminoglycan (including hyaluronan) carriers for use in the targeted drug delivery of poorly water soluble drugs. Following lipidation, the modified glycosaminoglycans are stated to self-assemble, forming spheres, wherein the hydrophilic portion of the glycosaminoglycan is on the outside surface and the hydrophobic lipid portion lies within the sheltered inner surface. Similar self-assembled nanospheres and microspheres have also been described by Margarlit and Peer (WO 03/015755), where it is taught that, depending on the amount of phospholipid bound to the hyaluronic acid, nanoparticles (~20% of linking sites occupied) or microparticles (~33% of linking sites occupied) could be formed.

Scott (EP 0295 092 B1), who highlights the difficulties of enabling the passage of hyaluronan through the skin, describes preparations of hyaluronic acid fragments comprising 7 to 50 monosaccharide units for topical application. Penetration through the skin barrier is aided through the addition of activity enhancers to the formulation, the use of liposomes formed from phosphatidylcholine as a delivery vehicle, or the use of a battery-operated iontophoresis patch. However, as noted by the selected range of hyaluronan preferred 7 to 25 monosaccharide units (approximately 1,300-4,700 Da) owing to the difficulty in delivering hyaluronan through the skin barrier, these formulations are unsuitable to enable the passage of higher molecular weight hyaluronan through the skin barrier.

Della Valle and Romeo (U.S. Pat. No. 4,851,521) describe the preparation of esters of hyaluronic acid for use in a variety of applications, including cosmetics and as tissue fillers, as well as for the preparation of films and threads. Although indicated for a variety of applications, there is no teaching provided that the modified hyaluronan compositions are able to transport hyaluronan through the skin barrier; rather, subcutaneous, and intradermal administrations are indicated.

Generally, the diffusion of substances through an epithelial barrier decreases sharply when the molecular weight exceeds 700 Da. Although Pinsky (WO 2009/086504) describes skin care compositions utilizing liposomes to deliver low molecular weight collagen fragments (8.5 kDa), and optionally hyaluronan, into the skin, there remains a need for methods to permit the dermal deliver of larger molecular weight collagens and elastins, as well as therapeutically useful peptides and proteins, particularly if these do not require the use and preparation of liposomes. Epithelial delivery techniques, including transdermal delivery, for peptides and proteins was recently reviewed by Antosava et al.,[17] who noted that although transdermal delivery is an attractive approach for development owing to its high bioavailability, long duration of action and painless application, it is hindered by the effectiveness of the skin barrier in preventing penetration and local irritation which preclude long-term application.

Although there are reports describing the use of phospholipid-based liposomes to transfer hyaluronan across the skin barrier, a number of problems are associated with their use, most notably, a lack of stability on storage. In addition, phospholipid-based liposomes are expensive to prepare and purify on the scale required for use in cosmetic preparations.

Despite the numerous reports in the patent literature of topically-applied cosmetic compositions containing hyaluronan that are stated to facilitate the passage of hyaluronan through the skin barrier into the epidermal and dermal layers, it remains that there are no commercially available cosmetic products fulfilling these promises. In particular, there are currently no viable methods with which effectively to deliver sufficient quantities of higher molecular weight hyaluronan (e.g., >250,000 Da) to the epidermal and dermal layers of the skin using topical cosmetic formulations that allow for retention of the hyaluronan within the skin. Rather, for cosmetic purposes, demand for the development of new filler products remains directed towards injectable hyaluronan fillers, such as Hyal-System™, or the use of hyaluronan as a surface filler that resides temporarily on the skin surface.

Therefore, one object of the present invention is to provide compositions that allow for the passage of a modified hyaluronan through the skin barrier to the epidermal and dermal layers of the skin, without requiring the use of injections, liposomes or other penetration enhancers.

A further object of the present invention is to provide modified hyaluronan compositions suitable for use in dermal enhancement, hyaluronan replenishment and/or protection therapy against the signs of aging of the skin and various forms of skin atrophy.

A further object of the invention is to provide modified hyaluronan compositions suitable for use in the reduction of scarring.

A further object of the invention is to provide modified hyaluronan that can increase the degree of hyaluronan retention in the extracellular coats of dermal cells despite the depletion or absence of hyaluronan receptors, such as CD44 and RHAMM, which are believed to be essential to hyaluronan retention, and are known to be depleted in aged and damaged skin.

A further object of the invention is to provide modified hyaluronan compositions that may be used as a topically administered carrier to deliver cosmetically and pharmaceutically active therapeutic substances through the skin barrier.

A further object of the invention is to provide modified hyaluronan compositions that may be used to topically deliver proteins, polypeptides and other large biomacromolecules (molecular weights of 700 Da to about 400-500 kDa) through the skin barrier.

A further objection of the invention is to provide modified glycosaminoglycan compositions that are able to penetrate the skin barrier for use in replenishing the levels of glycosaminoglycans within the skin, acting as hyaluronan mimetics, delivering cosmetically and therapeutically active substances, and delivering polypeptides, proteins and other large biomolecules.

A further object of the invention is to provide methods of manufacturing the above described modified glycosaminoglycan compositions wherein an activating agent is used as the limiting reagent to control the amount of lipid that is covalently bound to the glycosaminoglycan.

Further and other objects of the invention will be realized from the following Summary of the Invention, the Discussion of the Invention and the embodiments and Examples thereof.

SUMMARY OF THE INVENTION

Within the present invention, compositions are provided enabling the topical delivery of modified hyaluronan through the skin barrier, thereby providing an alternative mode of delivery to injectable hyaluronan-based fillers. By facilitating dermal delivery, the compositions of the present invention allow for the replenishment of hyaluronan throughout the depleted areas of the skin to which the compositions are applied, thereby providing a rejuvenating effect to the skin, one consequence of which is a reduction in the appearance of wrinkles, without requiring injections.

Further, the present invention provides a method for making, reviving, or supplementing the microenvironment around cells (cell coats) associated with youthful cells, thereby enhancing a youthful appearance in aged or repairing the damage done to traumatized skin.

The present invention also provides compositions which comprise hyaluronan and other glycosaminoglycans modified through the formation of covalent linkages with amphipathic lipids moieties, including phospholipids, glycerophospholipids, glycolipids, steroids, sphingolipids, glycosphingolipids, and fatty acids to about 1 to about 15% of the disaccharide monomer units, thus providing compositions allowing for dermal penetration of the modified glycosaminoglycan, together with methods for such modifications.

The present invention also provides for passage of the modified hyaluronan through the skin barrier is enabled through compositions comprising phospholipids covalently linked to hyaluronan.

The present invention also provides a non-toxic modified hyaluronan capable of crossing the skin barrier is provided that is suitable for use in dermal enhancement, hyaluronan replenishment and/or protection (e.g. moisture layer for aging or atrophic skin) therapy The present invention also provides compositions of a modified hyaluronan useful for the dermal and transdermal delivery of therapeutic substances, e.g., prostaglandins, which suppress inflammation, improve the smoothness and softness of skin and speed wound repair; delivery of peptiducins (therapeutic substances containing amino acids with lipid tails), which can regulate cell growth among their other functions; hyaluronidase inhibitors, which will assist in reducing the breakdown of hyaluronan in the skin; RHAMM inhibitors, which have been demonstrated to have an anti-wrinkle effect; and other peptides, peptide mimetics and proteins, such as a botulinum toxin, e.g., type A (BOTOX™), collagens, elastin, or hyaluronan synthases.

The present invention also provides a method for enhancing the level of hyaluronan within the skin, thereby making a more "youthful" microenvironment around epidermal and dermal cells, and resulting in control of cellular functions (e.g., collagen and elastin production by dermal cells; blocking transdifferentiation of dermal fibroblasts into myofibroblasts that produce scar type collagen I, contract the dermis and are thought to contribute to the formation of wrinkles; and activation of keratinocytes to produce cytokines and growth factors that promote dermal cell function), multilayering/proliferation of keratinocytes, protection against oxygen free radicals, and the retention of water that collectively enhances the youthful appearance of skin.

The present invention also provides non-toxic compositions comprising modified hyaluronan suitable for topical application to the skin to reduce the appearance of scarring, stretchmarks, burn contractions, fibrotic lesions, rosacea, dermatitis and skin atrophy due to exposure to UVA/B radiation, aging, chemotherapy, radiation therapy or steroid use.

The present invention also provides non-toxic compositions comprising modified hyaluronan fragments suitable for topical application to the skin that stimulate the innate immune system to protect against bacterial and viral infections of the skin and for promoting rapid recovering of large wounds (e.g. burns) by keratinocytes.

The present invention also provides a non-toxic modified hyaluronan composition that is able to cross the epidermal barrier, and is thus suitable for enhancing a regenerative type of wound repair, and for enhancing appearance of non-injured but compromised skin (e.g. smoker's skin) by promoting angiogenesis.

The present invention also provides compositions enabling for the passage of other modified glycosaminoglycans, such as dermatan sulfate, keratin sulfate and chondroitin sulfate in their polysaccharide or proteoglycan form as described above for hyaluronan. As would be understood, the choice of glycosaminoglycan to be used will depend on the treatment to be effected.

The present invention also provides compositions comprising modified hyaluronan or other glycosaminoglycans allowing for the dermal passage of polypeptides, such as collagen and elastin, for use in cosmetic application in the reduction in the appearance of wrinkles.

In a first aspect of the present invention is provided a glycosaminoglycan composition comprising a glycosaminoglycan modified through the covalent linkage of a lipid moiety to about 1-15% of the repeating disaccharide monomer units of the glycosaminoglycan wherein:

the glycosaminoglycan to be modified is hyaluronan, a hyaluronan derivative, a polysaccharide comprised of repeating disaccharide units of an uronic acid or hexose linked to a hexosamine, or derivatives thereof;

the glycosaminoglycan to be modified has a molecular weight in the range of about 2 kDa to about 2,500 kDa;

the lipid moiety comprises one or more naturally-occurring or synthetically-derived fatty acids, glycerolipids, phospholipids, sphingolipids, sterol lipids, prenol lipids, or derivatives thereof, provided that the lipid moiety contains a functional group on its polar headgroup to allow for covalent linkage of the lipid to the glycosaminoglycan; and the modified glycosaminoglycan is able to penetrate the skin barrier or a mucous membrane when applied thereto, whereby the modified glycosaminoglycan is formed by the reaction of the glycosaminoglycan with the lipid moiety.

In this aspect, preferably, the glycosaminoglycan is modified through the covalent linkage of a lipid moiety to about 1-12% of the repeating disaccharide monomer units of the glycosaminoglycan; more preferably to about 1-10% of the repeating disaccharide monomer units; even more preferably to about 1-7.5% of the repeating disaccharide monomer units; and most preferably to 2-6% of the repeating disaccharide monomer units. Exemplified compositions of the present invention include those wherein about 5.5% or about 6% of the repeating disaccharide monomer units have been modified. Preferably, the glycosaminoglycan to be modified has a molecular weight in the range of about 50 kDa to about 2,500 kDa; more preferably from about 100 kDa to about 2,000 kDa; even more preferably from about 350 kDa to about 1,500 kDa; and most preferably from about 500 kDa to about 1,500 kDa. Preferably, the glycosaminoglycan to be modified is hyaluronan or a hyaluronan derivative; more preferably, the glycosaminoglycan is hyaluronan. Preferably, the lipid moiety contains an amino group on its polar head-group and is covalently bound to the glycosaminoglycan via an amide linkage to a carboxylic acid group on the glycosaminoglycan; more preferably the lipid moiety comprises one or more phosphatidylethanolamines or phosphatidylserines; most preferably the lipid moiety comprises one or more phosphatidylethanolamines. Preferably, the modified glycosaminoglycan is able to penetrate the skin barrier. More preferably, the modified glycosaminoglycan has a longer residence time within the skin than the unmodified glycosaminoglycan, when dermally delivered; most preferably this glycosaminoglycan is hyaluronan.

In a second aspect of the present invention is provided a preparation suitable for application to the skin or a mucous membrane comprising a glycosaminoglycan composition in admixture with one or more cosmetically or pharmaceutically acceptable excipients or carriers, wherein the glycosaminoglycan composition comprises:

a glycosaminoglycan modified through the covalent linkage of lipid moieties to 1-15% of the repeating disaccharide units monomer units of the glycosaminoglycan;

the glycosaminoglycan comprises hyaluronan, a hyaluronan derivative, a polysaccharide comprised of repeating disaccharide units of an uronic acid or hexose linked to a hexosamine, or derivatives thereof;

the glycosaminoglycan to be modified has a molecular weight in the range of about 2 kDa to about 2,500 kDa;

the lipid moiety comprises one or more naturally-occurring or synthetically derived fatty acids, glycerolipids, phospholipids, sphingolipids, sterol lipids, prenol lipids, or derivatives thereof, provided that the lipid moiety contains a functional group on its polar head group to allow for covalent linkage of the lipid to the glycosaminoglycan; and the modified glycosaminoglycan is able to penetrate the skin barrier or mucous membrane when applied thereto, whereby the modified glycosaminoglycan is formed by the reaction of the glycosaminoglycan with the lipid moiety.

In this aspect, preferably, the glycosaminoglycan is modified through the covalent linkage of a lipid moiety to about 1-12% of the repeating disaccharide monomer units of the glycosaminoglycan; more preferably to about 1-10% of the repeating disaccharide monomer units; even more preferably to about 1-7.5% of the repeating disaccharide monomer units; and even more preferably to about 2-6% of the repeating disaccharide monomer units. Exemplified modifications of the present invention include those wherein about 5.5% or about 6% of the repeating disaccharide monomer units of the glycosaminoglycan have been modified. Preferably, the glycosaminoglycan to be modified has a molecular weight in the range of about 50 kDa to about 2,500 kDa; more preferably from about 100 kDa to about 2,000 kDa; even more preferably from about 350 kDa to about 1,500 kDa; and most preferably from about 500 kDa to about 1,500 kDa. Preferably, the glycosaminoglycan to be modified is hyaluronan or a hyaluronan derivative; more preferably, the glycosaminoglycan is hyaluronan. Preferably, the lipid moiety contains an amino group on its polar head-group and is covalently bound to the glycosaminoglycan via an amide linkage to a carboxylic acid group on the glycosaminoglycan; more preferably the lipid moiety comprises one or more phosphatidylethanolamines or phosphatidylserines; most preferably the lipid moiety comprises one or more phosphatidylethanolamines. Preferably, the modified glycosaminoglycan is able to penetrate the skin barrier. More preferably, the modified glycosaminoglycan has a longer residence time within the skin than the unmodified glycosaminoglycan, when dermally delivered.

Preparations of this aspect of the invention may additionally comprise one or more ingredients that are transported across the skin barrier or mucous membrane by the glycosaminoglycan composition; preferably across the skin barrier. Included among the additional the additional one or more ingredients that may be considered within this aspect of the invention are anti-oxidants, vitamins, essential oils, UV-blocking agents, or other nutrients whose application is known to provide a beneficial effect to the health or appearance of skin.

Also included among the additional the additional one or more ingredients that may be considered within this aspect of the invention are pharmaceuticals; preferably therapeutic agents suitable for the treatment inflammation, such as a prostaglandin, skin cancer or skin conditions that are delivered through the skin barrier.

Also included among the additional the additional one or more ingredients that may be considered within this aspect of the invention are proteins, peptides, peptide mimetics, pepducins, polynucleotides, or other biomolecules; preferably, these one or more ingredients have a molecular weight of between 700 Da and 500 kDa. Additional ingredients delivered across the skin barrier may include collagen or elastin. Additionally, the one or more additional ingredients may be a protein; preferably a botulinum toxin that is delivered across the skin barrier; more preferably botulinum toxin type A. A further preferred protein to be delivered across the skin barrier is hyaluronan synthase. The additional one or more ingredients may also include a pepducin.

Also included among the additional the additional one or more ingredients that may be considered within this aspect of the invention are hyaluronidase inhibitors delivered across the skin barrier or RHAMM inhibitors delivered across the skin barrier.

In a third aspect of the present invention is provided the use of a glycosaminoglycan composition of the above first aspect in supplementing the levels of a glycosaminoglycan naturally present in the skin; preferably this glycosaminoglycan is hyaluronan. This aspect includes the use of the compositions in the reduction in appearance of wrinkles, providing an increased level of skin hydration, reducing the signs of aging of the skin, the reversal in appearance or prevention of skin atrophy, the reversal in appearance or prevention of scarring on the skin, reducing the inflammation associated with actinic keratinoses, promoting angiogenesis (e.g., in regenerative wound repair or in enhancing the appearance of non-injured but compromised skin), and in reducing the effects of skin trauma. Among the effects of skin trauma that may be considered are reductions in the appearance of scarring, stretchmarks, burn contractions, fibrotic lesions, rosacea, dermatitis or skin atrophy. Among the causes of these trauma are the effects are UV radiation, burns, the topical administration of pharmaceuticals, and the use of steroids.

In a fourth aspect of the present invention is provided the use of a glycosaminoglycan composition of the above first aspect as a dermal or transdermal delivery vehicle for cosmetically and therapeutically active ingredients. Among the cosmetically and therapeutically active ingredients that may be delivered according to this aspect of the invention are hyaluronidase inhibitors, RHAMM inhibitors, collagen, or elastin. Also among the cosmetically and therapeutically active ingredients that may be delivered according to this aspect of the invention are proteins, peptides, peptide mimetics, pepducins, polynucleotides, or other biomolecules; preferably for the delivery of proteins. Preferred among the types of proteins that may be delivered are a botulinum toxin (preferably botulinum toxin type A) and hyaluronan synthase. Also among the cosmetically and therapeutically active ingredients that may be delivered according to this aspect of the invention are pharmaceuticals, such as anti-inflammatory agents (e.g., a prostaglandin). Preferred is the dermal delivery of pharmaceuticals. Among the preferred use for dermal delivery are included the delivery of pharmaceuticals useful in the treatment of skin inflammation, skin cancer, skin allergy, or other skin conditions; most preferably in the treatment of skin cancer.

In a fifth aspect of the present invention is provided a method for the glycosaminoglycan compositions of the above first aspect of the invention comprising the steps of:
treating the glycosaminoglycan to be modified with an activating agent to facilitate covalent bonding of the glycosaminoglycan to the lipid moiety;
mixing the activated glycosaminoglycan and lipid moiety; and
allowing the lipid moiety to react with the activated glycosaminoglycan to covalently link the lipid moiety to the glycosaminoglycan,
wherein the activating agent is the limiting reagent in the reaction and is added in an amount sufficient to facilitate covalent linkage of the lipid moiety to about 1 to about 15% of the disaccharide monomer units of the glycosaminoglycan.

In this aspect, preferably, the activating agent is added in an amount sufficient to facilitate covalent linkage of the lipid moiety to about 1-12% of the disaccharide monomer units of the glycosaminoglycan; more preferably to about 1-10% of the disaccharide monomer units; even more preferably to about 1-7.5% of the disaccharide monomer units; and most preferably to 2-6% of the disaccharide monomer units. Exemplified methods of the present invention include those wherein about 5.5% or about 6% of the repeating disaccharide monomer units have been modified.

According to this aspect of the invention, it is preferred that the covalent linkage to be formed is an amide linkage between a carboxylic group of the glycosaminoglycan and a lipid moiety containing an amine functional group on the polar head group. Preferably, the linking agent is a carbodiimide; more preferably, the carbodiimide is 1-ethyl-3-(3-dimethylaminopropyl)carbodiimide.

According to this aspect of the invention, the preferred glycosaminoglycan to be modified is hyaluronan.

According to this aspect of the invention it is preferred that the lipid moiety comprises one or more phosphatidylethanolamines and phosphatidylserines; more preferred is that the lipid moiety comprises one or more phosphatidylethanolamines.

Thus, included in this application is, in one aspect, an invention that promotes penetration of large hyaluronan into skin together with large (>10 kDa) proteins.

Without being bound by any theory of action, the inventor believes the hyaluronan-phospholipid formulation described herein promotes the formation of hyaluronan coats around skin in a receptor independent manner and prevents liposome/nanoparticle formation. As a result of both its direct integration into the cell membrane and its non-particulate nature (e.g. not a liposome or nanoparticle) it escapes detection/promotion of endocytic or pinocytic uptake by cells and therefore its rapid destruction. This escape results in increased residence time within the skin as intact hyaluronan-phospholipid.

BRIEF DESCRIPTION OF THE DRAWINGS

The following figures illustrate various aspects and preferred and alternative embodiments of the invention.

FIG. 1. Micrograph images of human dermal fibroblasts illustrating the increase in hyaluronan cell coat following application of a hyaluronan-phosphatidylethanolamine conjugate (HA-PE-1) of the present invention as compared to unmodified hyaluronan and PBS control. Representative hyaluronan cell coats are indicated by an arrow in each image.

FIG. 2. Graph illustrating the effect of a modified hyaluronan composition of the invention (HA-PE-1) on the percent of human fibroblasts with cell coats as compared to fibroblasts treated with hyaluronan alone untreated cells.

FIG. 3. Graph illustrating the effect of a modified hyaluronan composition of the invention (HA-PE-1) on the size of the hyaluronan cell coat as compared to cells treated with unmodified hyaluronan.

FIG. 4. Graph illustrating the difference in the number of mouse embryonic fibroblasts engineered to be without hyaluronan receptors (RHAMM−/−, CD44−/−, or RHAMM−/−:CD44−/−) that have hyaluronan coats following treatment with a hyaluronan-phosphatidylethanolamine conjugate (HA-PE-1) of the present invention, unmodified hyaluronan and saline solution (control). Representative micrograph images from treated fibroblasts are presented in FIG. 5.

FIG. 5. Representative micrograph images of mouse embryonic fibroblasts engineered to be without hyaluronan receptors (RHAMM−/−, CD44−/−, or RHAMM−/−:CD44−/−) that have hyaluronan coats following treatment with a hyaluronan-phosphatidylethanolamine conjugate (HA-PE-1) of the present invention, unmodified hyaluronan and saline solution (control).

FIG. 6. Micrographs of human fibroblasts treated with SKL catalase, a hyaluronan-phosphatidylethanolamine conjugate (HA-PE-1) and a combination of SKL catalase and HA-PE-1, demonstrating that the modified hyaluronan compositions of the invention enhance the effects SKL catalase when used in combination.

FIG. 7. Micrograph images of skin obtained from mice treated with a hyaluronan-phosphatidylethanolamine conjugate (HA-PE-1) of the present invention for four days illustrating the ability of the compositions of the present invention to penetrate the skin barrier following topical application. Images 71 (HA-PE-1) and 73 (control) illustrate the skin layer at 20× magnification with the keratinocyte layer denoted with "[". Images 72 (treatment) and 74 (control) illustrate the skin layer at 40× magnification with representative keratinocytes highlighted with an arrow.

Figure 7:
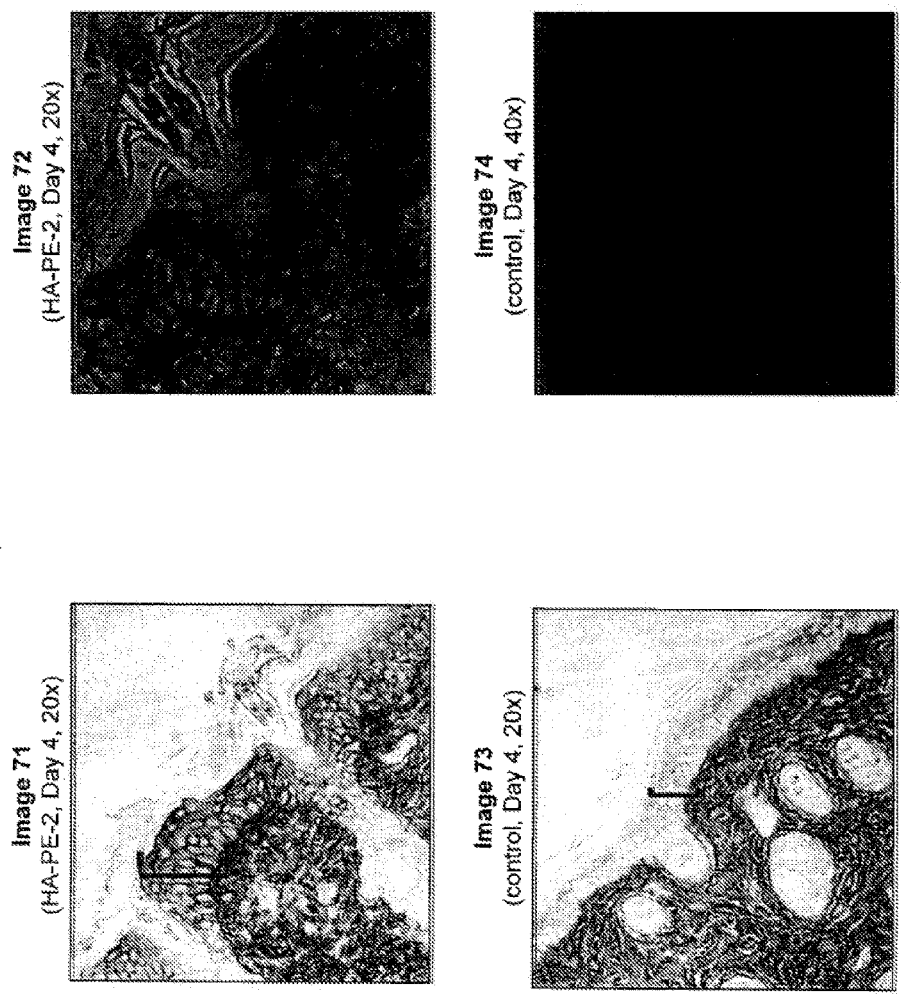
Figure 8:
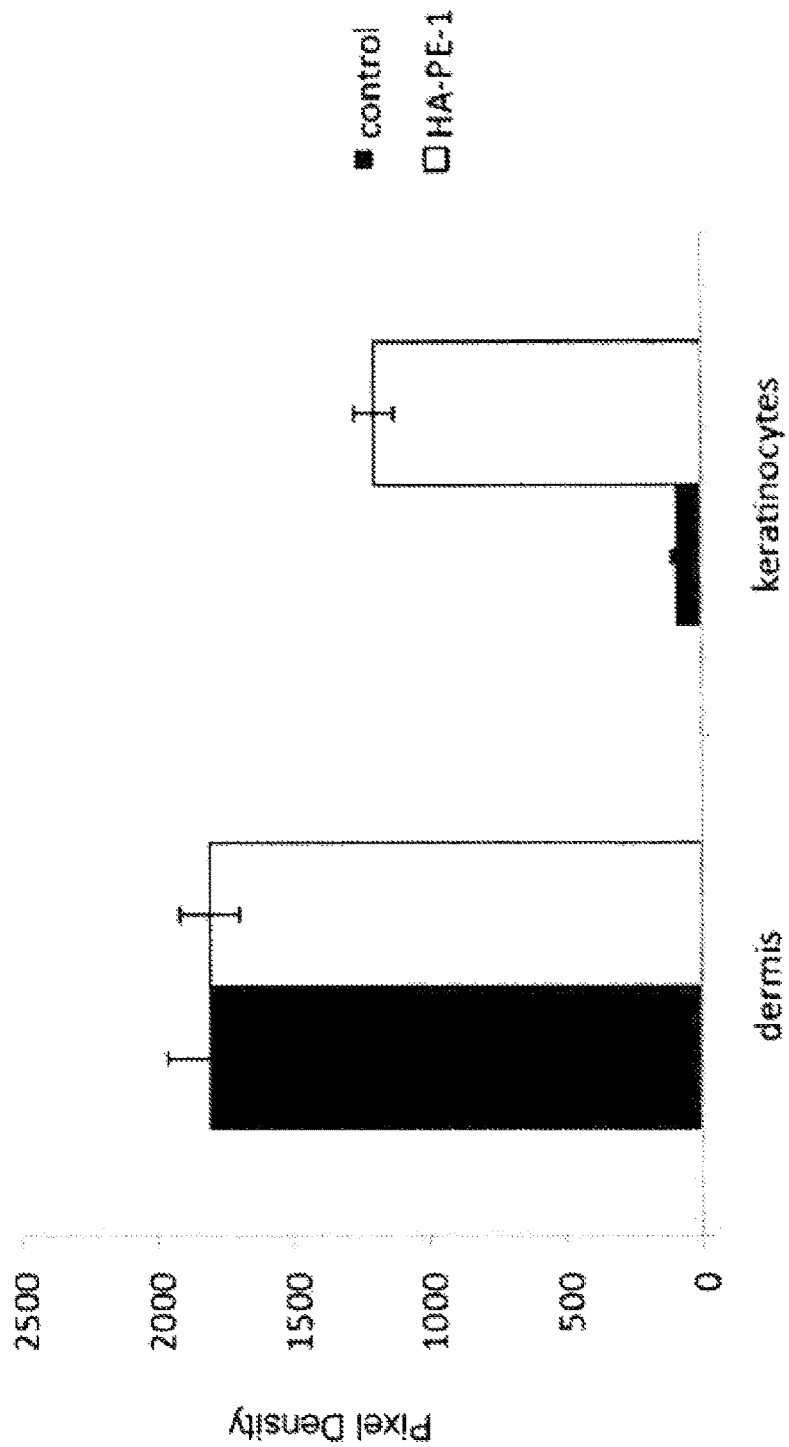

FIG. 8. Graph quantifying the ability of a cream containing a hyaluronan-phosphatidylethanolamine conjugate (HA-PE-1) of the present invention to penetrate the skin barrier of mice and be retained in the keratinocyte layer following 4 days of treatment. This graph quantifies the micrograph images presented in FIG. 7.

Figure 9:
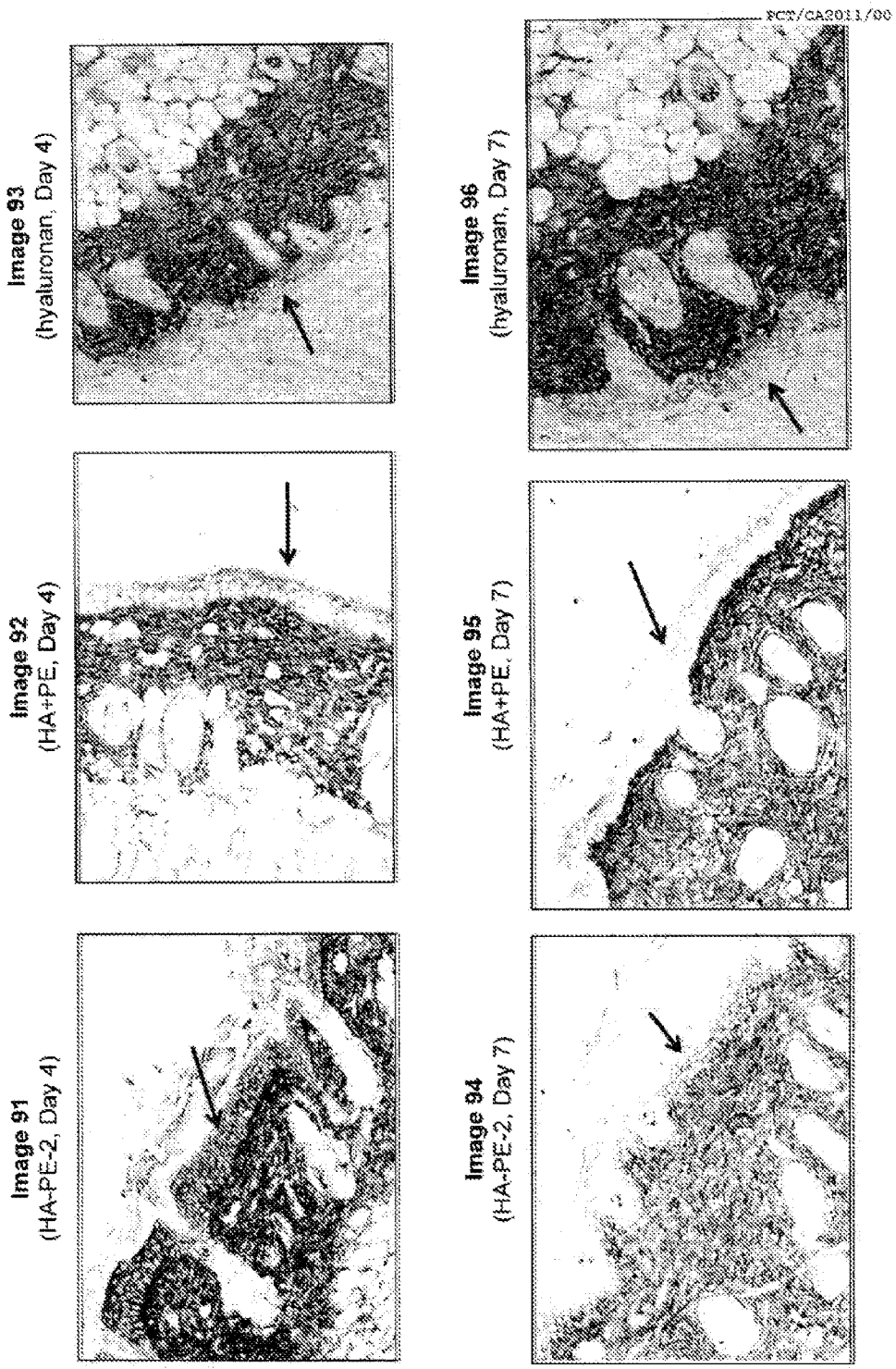

FIG. 9. Micrograph images comparing the skin of mice following a four-day treatment regimen with a hyaluronan-phosphatidylethanolamine conjugate (HA-PE-1) of the present invention, hyaluronan mixed with lecithin (HA+PE), or hyaluronan alone. The keratinocyte layer in each image is indicated with an arrow. Also presented are micrographs of skin samples obtained Day 7 following cessation of treatment on Day 4.

Figure 10:
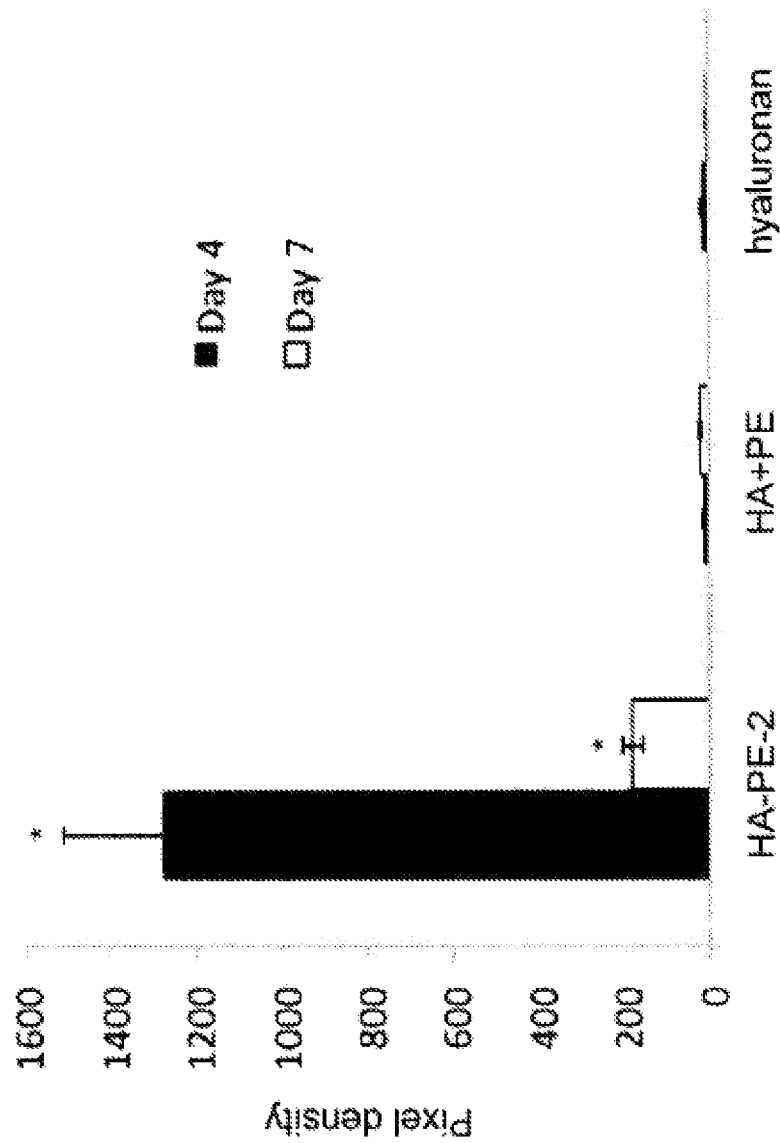

FIG. 10. Graph quantifying the amount of a hyaluronan-phosphatidylethanolamine conjugate (HA-PE-1) of the present invention that was able to penetrate mouse skin as compared to mice treated with a mixture of hyaluronan with lecithin (HA+PE) and hyaluronan alone. This graph quantifies the micrograph images presented in FIG. 9.

FIG. 11. Micrograph images demonstrating that application of the modified hyaluronan compositions of the present invention remains localized within the epidermis at the site of application. Application of hyaluronan alone does not lead to any accumulation of hyaluronan in the epidermis. The application edge is marked with an arrow, and application area with a broken-line arrow.

Figure 12:
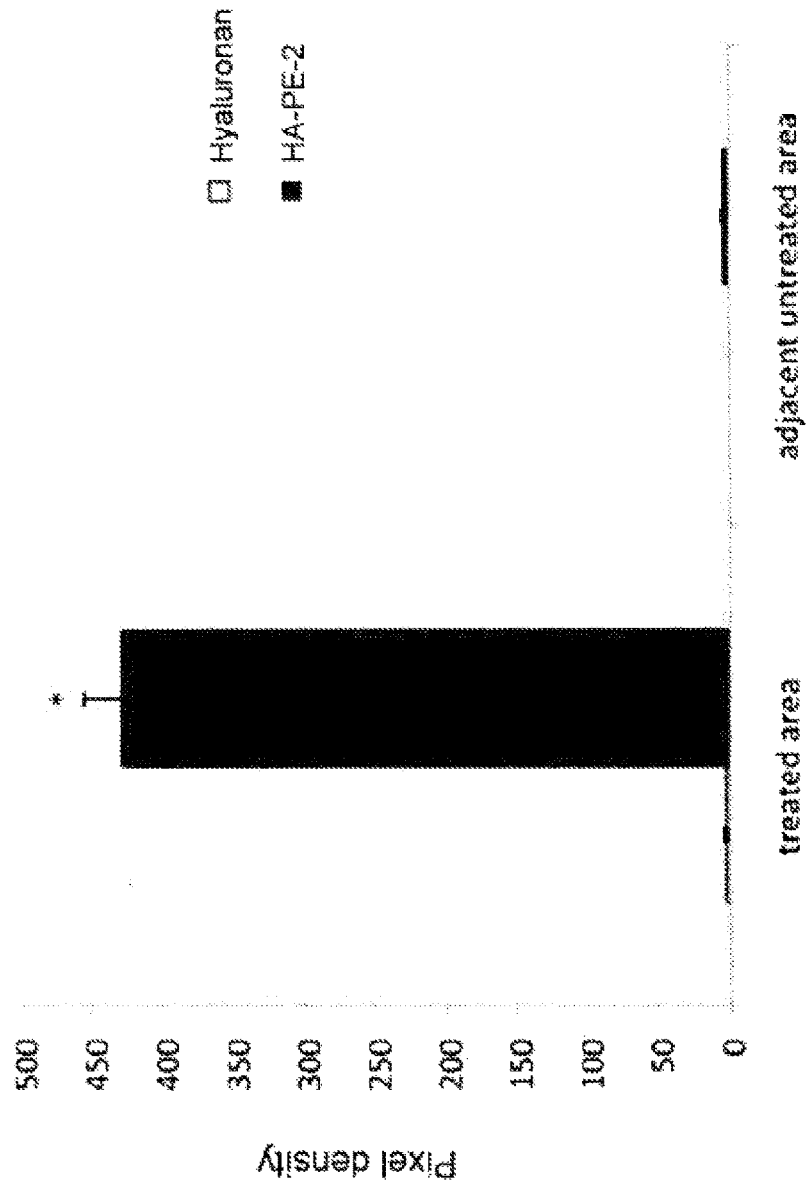

FIG. 12. Graph quantifying the levels of hyaluronan present in treated and untreated areas in mouse skin from FIG. 11.

FIG. 13. Micrograph images and quantifying graph indicating that the hyaluronan compositions of the invention (HA-PE-2) are able to penetrate the skin barrier and associate within the epidermis in mice bred without RHAMM hyaluronan receptors (RHAMM−/− mice). The keratinocyte layer in each image is denoted with an arrow.

Figure 14:
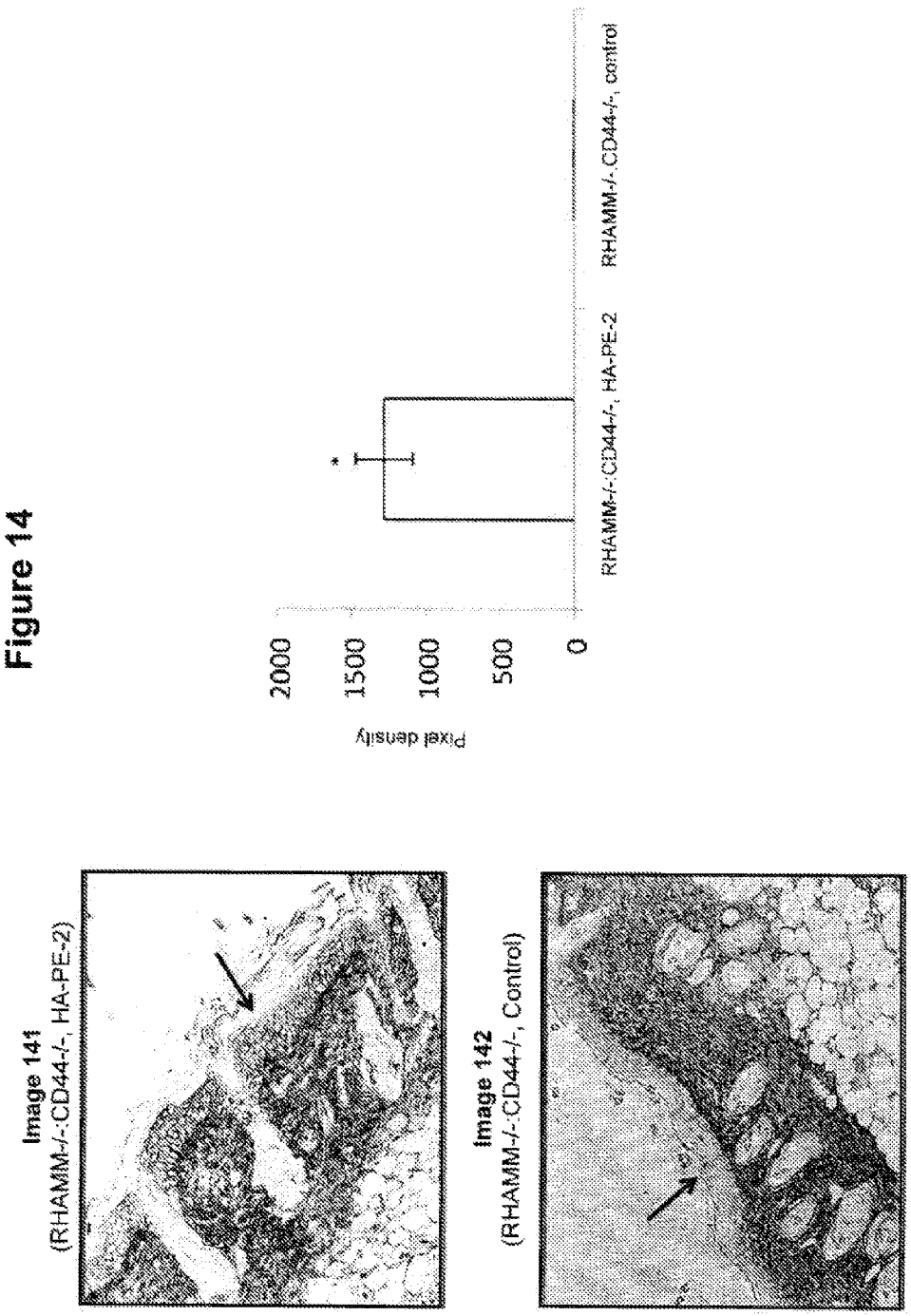

FIG. 14. Micrograph images and quantifying graph indicating that the hyaluronan compositions of the invention (HA-PE-2) are able to penetrate the skin barrier and associate within the epidermis in mice bred without RHAMM or CD44 hyaluronan receptors (RHAMM−/−:CD44−/− mice). The keratinocyte layer in each image is denoted with an arrow.

Figure 15:
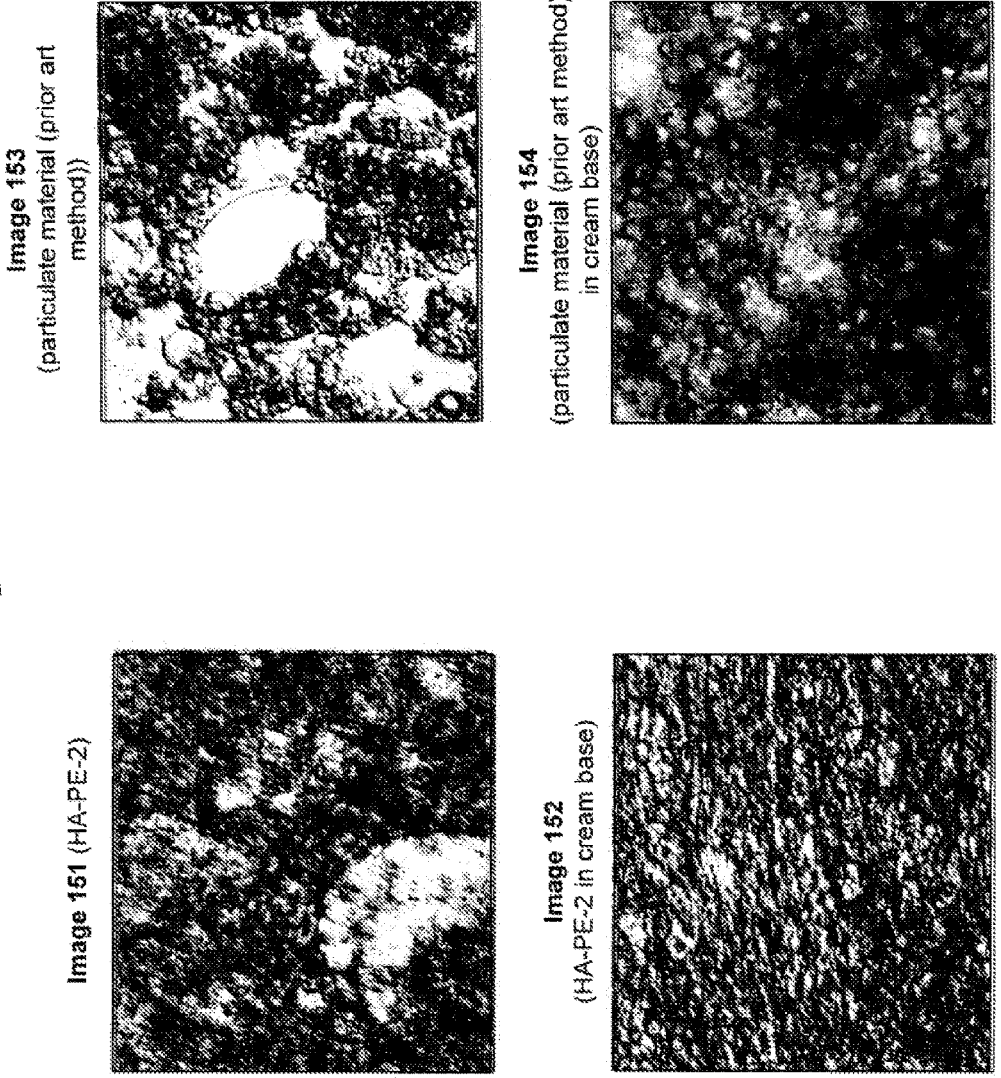

FIG. 15. Micrograph images of a hyaluronan-phosphatidylethanolamine conjugate (HA-PE-2) of the present invention and particulate lipidated glycosaminoglycans prepared using prior art methods.

Figure 16:
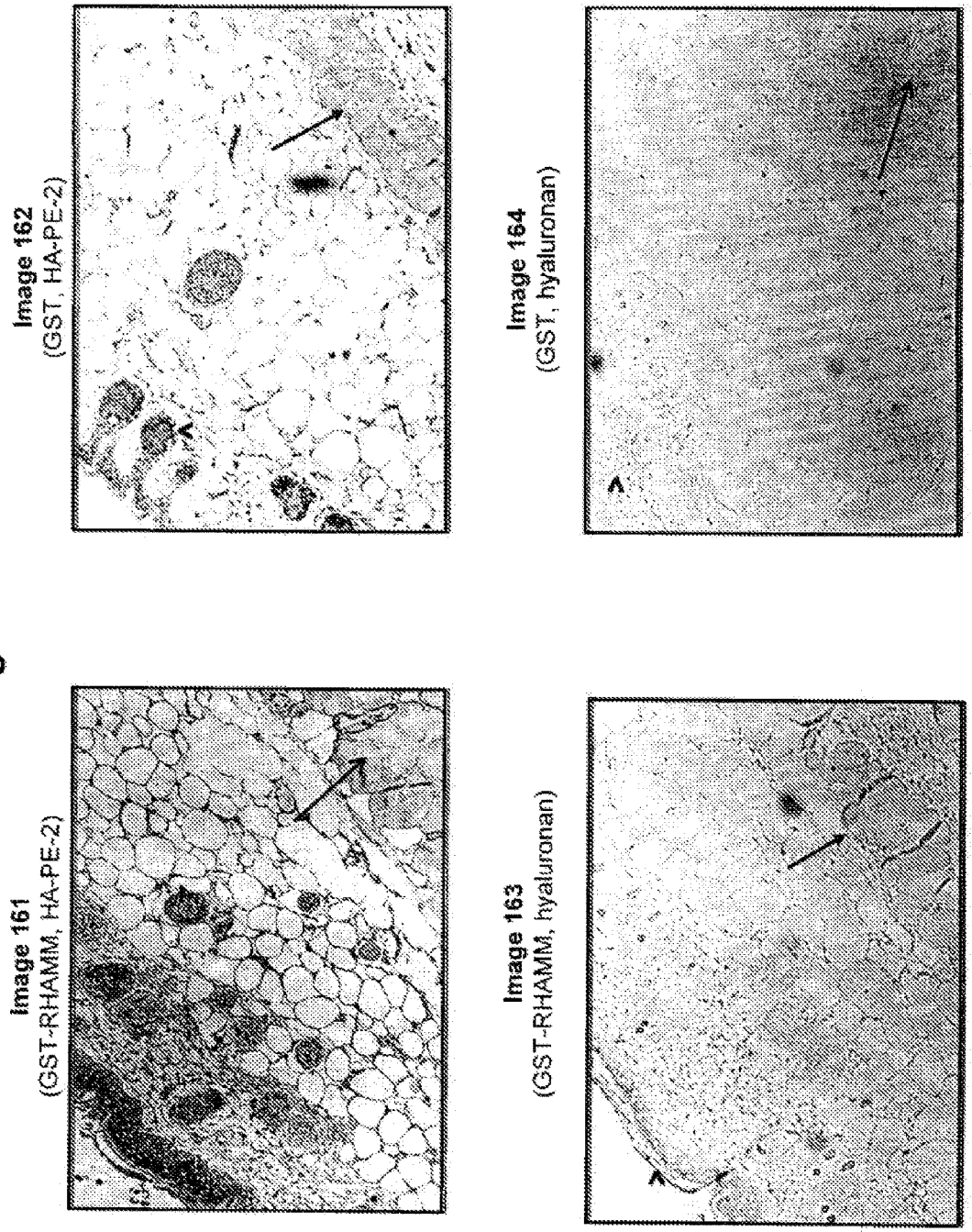

FIG. 16. Micrograph images demonstrating the ability of a hyaluronan-phosphatidylethanolamine conjugate (HA-PE-2) of the present invention to deliver an 84 kDa protein (GST-labelled RHAMM) and a 26 kDa protein (GST) through the skin barrier following topical application in mice. The keratinocyte layer is denoted by "∧" and the underlying muscle layer by an arrow.

FIG. 17. Graph quantifying the micrograph images of FIG. 16 for the delivery of GST-RHAMM, an 84 kDa protein, through the skin barrier following topical application of a hyaluronan-phosphatidylethanolamine conjugate (HA-PE-2) of the present invention to mice.

DESCRIPTION OF THE INVENTION

The present invention provides compositions that enable the passage of modified glycosaminoglycans through the skin barrier following topical administration, thus making them suitable for use in cosmetic formulations and as vehicles for the dermal and transdermal delivery of cosmetically and pharmaceutically active therapeutic agents. These glycosaminoglycan compositions are formed through the covalent linkage of a lipid moiety to the glycosaminoglycan by limiting the degree of linkage to about 1 to about 15% of the disaccharide monomer units in order to provide sufficient lipophilicity to the glycosaminoglycan to facilitate its passage through the skin barrier, while at the same time allowing for the maintenance of its glycosaminoglycan character, particularly its cellular interactions. Preferably, the degree of linkage is from about 1-12%, more preferably from about 1-10%, even more preferably from about 1-7.5%, and even more preferably from about 2-6% for example about 5.5% and about 6% of the disaccharide monomer units. One effective way to introduce the lipid moiety is through bonding at carboxylic acid groups situated throughout the glycosaminoglycan on its saccharide residues. When linking the lipid moiety to the glycosaminoglycan in the preparation of the present compositions, it is important to consider the percentage of available linking sites that are used. As taught by Margarlit and Peer (WO 03/015755), covalent linking of phosphatidylethanolamine at 20-33% of the available carboxylic acid sites provides compositions that self assemble to form particulate nanospheres or microspheres that can act as carriers for insoluble or poorly soluble compounds. Thus, in order to avoid the formation of these undesired particulate structures, it has been found to be necessary to use a lower degree of linking when preparing compositions of the present invention.

When preparing the modified glycosaminoglycan compositions of the present invention, the lipid moiety may be covalently linked to the glycosaminoglycan using any known manner, and may include, for example, linkages to the existing functional groups (e.g., carboxylic acid and hydroxy) or to unmasked functional groups (e.g., through the partial hydrolysis of N-acetyl groups to provide primary amines). While any form of covalent linkage may be used between the glycosaminoglycan and lipid moiety, it is generally preferred that the linkage is hydrolyzable within the body, e.g., amide and ester linkages, so that the modified glycosaminoglycan may be reverted to its natural form, thus facilitating its ultimate bioresorption, and reducing the potential for toxic and/or allergenic reactions, when glycosaminoglycans and lipids that are naturally present in the skin are used.

The glycosaminoglycan compositions of the present invention are preferably prepared using hyaluronan, although other glycosaminoglycans, particularly hyaluronan derivatives, including partially N-deacetylated hyaluronan, may also be used. Although, with the exception of hyaluronan, naturally occurring glycosaminoglycans are attached to proteins, use of the term glycosaminoglycan in the context of the present invention refers to the polysaccharide portion of glycosaminoglycans only. Glycosaminoglycans suitable for use in the compositions of the present invention include any long, unbranched polysaccharides comprised primarily of a repeating disaccharide unit comprised of an uronic acid or hexose linked to a hexosamine, provided the size requirements described below are met.

Hyaluronan is present in high levels in the skin and, when the compositions of the present invention are used as delivery devices for cosmetic and pharmaceutical therapeutic agents, including proteins and similarly sized biomacromolecules, a dual effect comprising delivery of the therapeutic agent and enhancement of hyaluronan cell coats in the treated area may be obtained. This dual effect can be of particular advantage when the topical delivery of a therapeutic agent has previously been associated with damage to the skin at the application site as may be observed, for example, with the topical treatment of glucocorticoids, which is known to reduce the levels of dermal hyaluronan.[18] A further reason for the preference for the use of hyaluronan over other naturally-occurring glycosaminoglycans in the skin (e.g., heparin sulfate, dermatin sulfate, keratin sulfate, or chondroitin sulfate) is its ease of access in high (>100 kDa) molecular weights through biosynthetic means using bacteria, thus making its supply independent of animal sources and, as a result, less prone to allergenic issues associated with animal-derived materials.

The glycosaminoglycan used in the present invention will typically possess a molecular weight of between about 50 kDa and about 2,500 kDa, and is preferably in the range of about 100 kDa to about 2,000 kDa. More preferably, the glycosaminoglycan has a molecular weight of about 350-1,500 kDa, and most preferably of about 500-1,500 kDa. However, for specific medical uses in wounds, such as the promotion of innate immunity, angiogenesis and resurfacing of wounds, the optimal hyaluronan size is smaller, since fragmented hyaluronan is more bioactive than native hyaluronan and can be in the range of about 2 to about 100 kDa.

The lipid moiety of the present compositions may be comprised of one or more lipids, preferably those selected from the classes of fatty acids, glycerolipids, phospholipids, sphingolipids, sterol lipids and prenol lipids. Although it is a requirement of the present invention that the lipid moiety is covalently bound to the glycosaminoglycan, compositions of the present invention may include the lipidated glycosaminoglycan as well additional lipids that are not covalently bound.

The only requirement for the use of a given lipid in modifying the glycosaminoglycan is that it has the ability to be covalently bound to the glycosaminoglycan through its polar head group. While the use of lipids naturally present in the human or animal to be treated is preferred, derivatized forms of naturally occurring lipids may also be used provided that their lipid-character is maintained. Such derivatization may be required when the available functional groups on the polar head group of the lipid will not allow for linking of the lipid to the glycosaminoglycan. Examples of derivatized lipids include those that are modified to facilitate the bonding of the lipid to the glycosaminoglycan, e.g., through the addition of a primary amine to the polar head group of the lipid. Further examples include modifications to the hydrophobic tail of the lipid, provided that the lipophilic character of this region is preserved. Additionally, stereoisomers of naturally occurring lipids may also be used, with further derivatization if necessary to facilitate bonding to the glycosaminoglycan. The methods of performing any required modifications to the lipids are well known to persons skilled in the art.

In general, any fatty acid, either alone or as part of a group of fatty acids or other lipids, may be used in the compositions of the present invention, with those possessing greater than 12 carbon atoms being preferred, and include saturated, monounsaturated and polyunsaturated fatty acids. Although there is a preference for the use of fatty acids that are naturally occurring in humans, this preference is in terms of bioresorption of the compositions, and in their lower potential for toxic and/or allergenic side effects, rather than their ability to pass through the skin barrier. Preferably the fatty acid used, either alone or as a component of a larger lipid, contains 12-24 carbon atoms. The following are non-limiting examples of fatty acids that may be used in the compositions of the present invention, either alone or as part of a larger lipid: myristic (12:0, tetradecanoic), palmitic (16:0, hexadecanoic), stearic (18:0, octadecanoic), arachidic (20:0, eicosanoic), and behenic (22:0, docosanoic) saturated fatty acids; palmitoleic (16:1(n-7), cis-9-hexadecenoic), petroselinic (18:1(n-12), cis-6-octadecenoic), oleic (18:1(n-9), cis-octadecenoic, cis-vaccenic (18:1(n-7), cis-11-octadecenoic), erucic (22:1(n-9), cis-13-docosenoic monounsaturated fatty acids; and linoleic (18:2(n-6), 9,12-octadecadienoic), γ-linolenic (18:3(n-6), 6,9,12-octadecatrienoic), α-linolenic (18:3(n-3), 9,12,15-octatrienoic), arachidonic (20:4(n-6), 5,8,11,14,17-eicosatetraenoic), EPA (20:5(n-3), 5,8,11,14,17-eicosapentaenoic), and DHA (22:6(n-3), 4,7,10,13,16,19-docosahexaenoic) polyunsaturated acids. In addition to being used in their natural form, the above fatty acids may be modified to better facilitate covalent or noncovalent binding to the glycosaminoglycan by, for example, converting the acid head group to an alcohol or amine, an alcohol further derivatized as a leaving group, or a leaving group. As well, the fatty acid may be derivatized by adding a short spacer, e.g., formation of esters with 2-aminoethanol, ethylene glycol or other ethanol derivatives possessing a desired functional group. All chemistry required to prepare such modified fatty acids are believed to be routine and known by chemists skilled in organic synthesis. As should be apparent, the use of essential fatty acids, i.e., those fatty acids that are not produced in human tissues and must be acquired through the diet, such as arachidonic, linoleic and linolenic acids and their metabolites such as EPA and DHA, among others, may, in addition to their function in the present invention, provide an additional source of these nutrients separate from the diet following their use in the delivery of hyaluronan through the skin barrier as the compositions of the present invention are biodegraded. The use of essential fatty acids may be on their own, as part of a larger lipid, or as an auxiliary lipid that is not covalently bound to the lipidated glycosaminoglycan but is instead dermally or transdermally delivered by the lipidated glycosaminoglycan. Fatty acid derivatives with substituents or branching along the carbon chain may also be used in the present invention provided that the lipid character of the derivatized fatty acid is maintained.

Further fatty acids useful in the compositions of the present invention include branched chain fatty acids possessing from 10 to 30 carbon atoms. Branches may include one or more methyl groups substituted at any position along the saturated or unsaturated fatty acid chain, or involve larger alkyl groups. Other useful fatty acids include those with one or more alicyclic rings along the fatty acid backbone or at a terminal position. Further useful fatty acids also include hydroxy fatty acids, wherein the hydroxy group is within two carbons of the carboxylic acid (α- and β-hydroxy fatty acids). The α- or β-hydroxy group of the hydroxy fatty acids may also be further derivatized through the formation of ethers or ester to add a second fatty acid chain to the lipid, thereby increasing its lipophilic character.

The preceding discussion of fatty acids also applies to their use in the following types of lipids where the lipids contain fatty acid components.

In addition to the use of fatty acids, suitable lipids for use in the present invention also include fatty amides, the amide analogues of fatty acids. Preferred fatty amides are those in which a fatty acid is converted to an amide by, for example, treatment with 2-aminoethanol, thus providing an alcohol that may be further modified, if desired. Similarly, fatty amides can be formed using diamines, such as 1,2-diaminoethane, thus providing a primary amine for facilitating linkage to the glycosaminoglycan. Suitable fatty amides may also be formed using fatty acids and amino acids, which may then be further derivatized, if desired. Preferred fatty amides include anandamide, which is known to exhibit anti-inflammatory and anti-cancer properties, N-arachidonoylglycine, and N-palmitoylethanolamide, which may also have use in treating inflammation. The use of such fatty amides, among others with therapeutic effects, enable to the provision of dual effects, e.g., facilitating the transport of the glycosaminoglycan through the skin barrier and providing their known therapeutic effects following hydrolysis from the lipidated glycosaminoglycan within the body.

Glycerolipids that may be used in the present invention include mono- and diacylglycerolipids. Preferred glycerolipids are mono- and diacylglycerols and glycosylglycerols. More preferred are those glycerolipids possessing a fatty acids selected from the preferred groups mentioned above. Also preferred are glycerolipids that may act as intermediates in the biosynthesis of triacylglycerols and other lipids; however this preference is based upon their ability to provide further effect upon hydrolysis from the lipidated glycosaminoglycans of the present invention rather than their ability to facilitate penetration of the skin barrier. Depending upon the type of bond formation with the glycosaminoglycan that is desired, the glycerolipid may also be further derivatized, for example, through the use of a spacer, or direct derivatization, to provide a primary amino group, allowing for amide formation with the carboxylic acid groups of the glycosaminoglycan.

Phospholipids suitable for use in the compositions of the present invention include phosphatidylethanolamines (cephalins), phosphatidylserines, phosphatidyl-L-threonines, phosphatidylglycerols, phosphatidylinositols, phosphatidic acids, bisphosphatidyl glycerols (cardiolipins), and phosphoglycolipids. Preferred among the types of phospholipids are phosphatidylethanolamines, phosphatidylinositols and phosphatidylserines. More preferred are phosphatidylethanolamines and phosphatidylserines. Most preferred are phosphatidylethanolamines. While naturally occurring phospholipids are preferred owing to considerations of bioresorption rather than facilitating skin penetration, non-naturally occurring phospholipids may also be used. Non-naturally occurring phospholipids includes phospholipids that are derivatized versions of phospholipids that are not suitable for linking to the glycosaminoglycan, such as phosphatidylcholines, wherein the derivatization provides a functional group to enable covalent linkage of the lipid to the glycosaminoglycan. In addition to being in their traditional diacyl forms, suitable phospholipids may also include ether phospholipids, e.g., alkylacyl phospholipids and alkenylacyl phospholipids. Also suitable for use in the present invention are the lysophospholipids of any of the above phospholipids in which one of the fatty acid chains has be hydrolyzed to give a monoacyl, monoalkyl or monoalkenyl phospholipid. Suitable phospholipids may also be modified at their head group provided that this either enhances or does not preclude the covalent linking of the phospholipid to the glycosaminoglycan.

Sphingolipids suitable for use in the compositions of the present invention include sphingosine and other sphingoid bases, ceramides, ceramide phospholipids, and glycosphingolipids. For purposes of the present invention, ceramide phospholipids refers to those sphingolipids other than sphingomyelin in which a ceramide is bound to a phosphate group, and includes sphingolipids such as ceramide phosphorylethanolamines, ceramide phosphorylglycerols, ceramide inositols, and similar classes. Suitable sphingoid bases, for use either alone as a sphingolipid or as a component of a ceramide, ceramide phospholipid, sphingomyelin, glycosphingolipid, or other sphingolipid, may also include analogues of sphingoid bases with differing carbon chains (length, unsaturation, hydroxylation), but preferably those with 14-24 carbon atoms. Preferred sphingoid bases, for use either alone as a sphingolipid or as a component of a ceramide, ceramide phospholipid, glycosphingolipid or other sphingolipid, include sphingosine (d18:1, d18:1$^{\Delta 4t}$, 4E-d18:1, or its cis isomer: d18:1$^{\Delta 4c}$, 4Z-d18:1) dihydrosphingosine (d18:0, sphinganine), phytosphingosine (t18:0), and dehydrophytosphingosine (t18:1, t18:1$^{\Delta 8t}$, 8E-t18:1, or is cis isomer: t18:1$^{\Delta 8c}$, 8Z-t18:1), and eicosasphingosine (d20:1, 4E-d20:1, d20:1$^{\Delta 4t}$). As for the classes of lipids described above, preferred among the sphingolipids are those that are naturally occurring. Preferred types of sphingolipids include ceramide phosphorylethanolamines, ceramide phosphorylinositols, and monoglycosphingolipids. Suitable sphingolipids may also include ones in which an ethanolamine, serine or other suitable group is bound directly to the ceramide. Other preferred sphingolipids include glycososphingolipids, which are modified on the sugar group to also include phosphorylethanolamine, phosphorylserine, phosphonoethanolamine, serine or ethanolamine. Since sphingolipids are known in nature to have different fatty acids than glycerol-based lipids, such as those described above, the fatty acids preferred in sphingolipids may differ from the general description of fatty acids provided above. Thus, for sphingolipids, preferred fatty acids may have up to 28 carbons, and have an even or odd number of carbons. Of these fatty acids, which may be saturated, monounsaturated, or polyunsaturated, those with 16-24 carbons being saturated or monounsaturated are preferred.

In addition to phosphatidic acid-based phospholipids and sphingolipids described above, the compositions of the present invention may also utilize the analogous phosphonolipids, such as phosphonylethanolamines and phosphonyl-1-hydroxy-2-aminoethanes; preferred phosphonolipids are phosphonylethanolamines.

Since ceramides are natural components of skin, and their depletion with age or disease results in skin dehydration, wrinkles/sagging, and susceptibility to disease, the use of ceramides and ceramide-based lipids that can be hydrolyzed into ceramides in the skin provides a dual benefit. The use of ceramide-based lipids that can be hydrolyzed into ceramides within the skin in the compositions of the invention both assists in the delivery of hyaluronan through the skin barrier, as well as provides a source to aid in the replenishment of ceramide levels upon degradation of the compositions.

Sterol lipids suitable for use in the compositions of the invention include sterols and oxysterols in which the A or B ring of the cholesterol is oxidized rather than the alkyl chain, such as 7β-hydroxycholesterol or 4β-hydroxycholesterol. Oxysterols in which the alkyl side chain has been hydroxylated, and optionally converted to an amine, are also suitable for use provided that the A and B rings of the cholesterol skeleton are in a reduced form, i.e., dehydroxylated. Oxysterols possessing a primary hydroxy group that is oxidized to a carboxylic acid may also be used, particularly when esterified with 2-aminoethanol, to provide a terminal amino group to facilitate binding to the glycosaminoglycan. In addition to the sterols commonly found in mammals, sterols from other origins, such as plant-based sterols (phytosterols), may also be used in the compositions of the present invention. Useful phytosterols include, but are not limited to, campesterol, sitosterol, brassicasterol, stigmasterol, avenasterol. Sterols may also be derivatized by adding, for example, 2-aminoethanol, inositol, serine, glycoside, phosphorylethanolamine, phosphonylethanolamine, phosphorylserine, phosphorylinositol, phosphorylglycosides, or glycosides derivatized with 2-aminoethanol, serine, phosphorylethanolamine, or phosphonylethanolamine, to the 3-hydroxy substituent of the A-ring or a hydroxy substituent of the alkyl side chain of any of the above sterols or oxysterols. Additionally, esters may be formed with amino acids to provide an amino group to facilitate binding to the glycosaminoglycan.

The use of 7-dehydrocholesterol can provide the additional benefit of being converted to vitamin $D_3$ (cholecalciferol) upon UV exposure following its penetration into the epidermal layer of the skin. Alternatively, cholecalciferol, or its precursor provitamin $D_3$, may be used directly as a lipid. Similar benefits would also be obtained through the use of the ergosterol, viosterol or ergocalciferol (vitamin $D_2$), or sitocalciferol (vitamin $D_5$), which is made from 7-dehydrositosterol upon UV irradiation. As a result, the lipid moieties used in modifying glycosaminoglycans for the present invention may also serve as delivery vehicles for the biologically important lipids as the modified glycosaminoglycans degrade within the body (provided a hydrolyzable linkage is used that will allow for release of the lipid in physiological conditions). When any of the above are used as lipids in the compositions of the present invention, the amounts used with respect to other lipids may be varied according to the amounts of vitamin D supplementation that is desired following its hydrolysis from the glycosaminoglycan.

In addition to sterol-derived Vitamin D, compositions of the present invention may also utilize other fat-soluble vitamins, such as vitamins A and E, and other prenol lipids, including other tocopherols, tocotrienols, retinoic acid, dolichols and polyprenols possessing functional groups to facilitate linkage to the glycosaminoglycan. Such lipids may also be further derivatized by, for example, adding 2-aminoethanol, inositol, serine, glycoside, phosporylethanolamine, phosphonylethanolamine, phosphorylserine, phosphorylinositol, phosphorylglycosides, or glycosides derivatized with 2-aminoethanol, serine, phosphorylethanolamine, or phosphonylethanolamine, to an available hydroxy substituent. Additionally, esters may be formed with amino acids to provide an amino group to facilitate binding to the glycosaminoglycan. As is the case for the use of any lipid capable of providing a biological response following its cleavage from the glycosaminoglycan, the amount used in any preparation will be determined by the amount of the lipid that is desired to be provided. Also useful are diphosphate derivatives of prenols, such as farnesyl pyrophosphate and presqualene diphosphate, which are used in the biosynthesis of sterols. Preferred prenol lipids include tocopherols (which includes vitamin E) and tocotrienols that are additionally able to act as antioxidants following the passage through the skin barrier, as well as vitamin A, or more preferably its oxidized form, retinoic acid, which is known to stimulate collagen production in skin, as well as farnesol lipids that are known to contribute to the lipid outer layer of the epidermis. The presence of antioxidants in the skin can further assist in preventing the breakdown of hyaluronan, whether naturally occurring or provided through the compositions of the present invention.

As mentioned above, most preferred among the lipids are those which are naturally occurring in humans, however, this preference is based upon their ability to be easily bioresorbed, and their lower potential for toxic and/or allergenic side effects, rather than their ability to facilitate penetration of the glycosaminoglycan through the skin barrier. The compositions of the present invention are intended for cosmetic and therapeutic use, and it is therefore desirable that the compositions do not exhibit significant toxicity as the lipids are gradually hydrolyzed within the body. As a result, prior to the use of a particular lipid, testing may be undertaken to determine whether a particular lipid is associated with a toxic effect, allergenic-type response, or irritation when released within the skin. Since many of the lipids useful in the compositions of the present invention are known to have biological effects in humans, the amount of any particular lipid used may be modified to either utilize or avoid such effects depending upon any benchmarks set for the use of the compositions.

More preferred among the lipid classes are phospholipids or sphingolipids selected from the group consisting of phosphatidylethanolamines, phosphatidylserines, phosphatidylinositols, sphingosines, ceramides, and ceramide-based lipids. Most preferred is the use of phosphatidylethanolamines.

In addition to glycosaminoglycans that are modified through the addition of one type of lipid, the glycosaminoglycan compositions of the present invention also include those in which two or more different types of lipids are added. This could include, for example, the addition of phosphatidylethanolamines possessing different fatty acids in the lipophilic tail portion, or the addition of phosphatidylethanolamines and ceramide-based lipids, i.e., different classes of lipids bound to the same glycosaminoglycan.

Preferably, the lipid to be covalently linked to the glycosaminoglycan possesses a primary amino group to facilitate amide formation with carboxylic acid groups present on monosaccharide units of the glycosaminoglycan. Alternatively, other preferred classes of lipids may possess a hydroxy group that is able to form an ester linkage with the carboxy group of the glycosaminoglycan, or a carboxylic acid group to form either an ester linkage with the hydroxy groups of the glycosaminoglycan, or an amide linkage with the an amino group on the glycosaminoglycan (present as part of a partially deacetylated or unacetylated glycosaminoglycan). In addition to the preferred forms of linking the lipid to the glycosaminoglycan discussed above, bonding may also be accomplished by other known methods known to skilled persons; however, these forms are less preferred.

A preferred linkage is formed between the carboxylic acid group of the glycosaminoglycan and an amino group of the lipid through an amide bond. Such bonds may be readily formed using the carbodiimide approach as taught in the art for similar covalently-bound lipid/glycosaminoglycan systems (e.g., Sakurai et al. in U.S. Pat. No. 5,464,942, Yerushalmi et al. in WO 2006/050246, or Margarlit and Peer in WO 03/015755). The main difference between the application of this carbodiimide approach in the preparation of the present compositions with those previously used in the art lies in the simplified procedure, using a lesser amount of the linking agent and not requiring the use of organic solvents, although they may be used, if desired. It is believed that conducting the coupling reactions in aqueous solutions, in the absence, or reduced amounts, of organic solvents, and using lesser amounts of the linking reagent both limits the degree to which the lipid portion is bound to the glycosaminoglycan, thereby preventing the formation of undesired particulate nano- and microspheres at higher (>20% substitution rates), as well as reducing the amount of potentially allergenic components (e.g., decomposed linker and by-products from the linking reaction) that may reside in the final product.

The simplified general procedure used in preparing lipidated glycosaminoglycans through the formation of amide bonds, as further exemplified for hyaluronan in Example 2 and Example 3, comprises:

(i) Mixing an aqueous solution containing the glycosaminoglycan with the lipid or lipid-containing mixture (dissolved in water or a water-miscible semi-miscible solvent), optionally with heating;

(ii) Adding the linking agent, e.g., a carbodiimide, in an amount such that it is the limiting reagent to control the amount of lipid linkage; and (iii) Allowing the coupling to take place with mixing over a period of 30 minutes to 3 hours.

In the method used in the following examples, the linking agent, a carbodiimide to facilitate amide formation, is the limiting reagent, being added in an amount based upon the desired percentage of lipid molecules to be attached to each chain. The lipid is generally added in molar excess, preferably a large excess, of the amount of linker used so that the degree of lipid attachment is controlled by the amount of the linking agent used. Thus, the amount of linking agent used represents the theoretical maximum of the amount of lipid that will be covalently bound to the glycosaminoglycan. As a result, it is be desirable to use recently purchased, freshly purified and/or recently assayed linking reagents when preparing compositions of the present invention to more accurately control the amount maximum amount of lipid that can be bonded to the glycosaminoglycan in a given preparation.

In addition, the use of the linking reagent, e.g., carbodiimide for use in amide formation, as the limiting reagent in the reagent, as well as minimizing or eliminating the use of organic solvents, can be useful in reducing the potential for allergenic responses when the compositions are applied to the skin. Following the linkage of the lipid moiety to the glycosaminoglycan, the composition prepared may optionally be purified, if desired, using any convenient method, to removed residual linking agent, decomposition products, and/or by-products from the linking reaction. Purification of the linked compositions is expected to further reduce the expected low potential of allergenic responses to the topical application of the compositions of the present invention. If desired, the purified compositions may be further reacted with one or more lipids in further lipid-linking steps to provide modified glycosaminoglycans possessing multiple lipids and/or lipids bound to the glycosaminoglycan by different methods. It may also be desired to prepare compositions additionally including non-covalently bound lipids to assist in the transport of the compositions through the skin barrier.

An alternative method of linking the carboxylic acid groups present in the saccharide units of the glycosaminoglycan with the lipid can involve the formation of ester bonds using any traditional method of ester formation, including the an approach similar to that taught by della Valle in U.S. Pat. No. 4,851,521. Applications of this approach would be suitable for the use of derivatized lipids containing a leaving group on the hydrophilic portion of the lipid, e.g., iodo that may be displaced by an oxygen of the carboxylate group of the glycosaminoglycan to form an ester. As for the use of the carbodiimide amide linkages discussed previously, the main modification to the procedures of della Valle involve the ratios of glycosaminoglycan to lipid used.

In addition to the above methods, any other suitable method may be used to covalently link the lipid moieties to the glycosaminoglycan. Suitable methods are determined based upon the available functional groups of the glycosaminoglycan, the available function groups of the lipid, and the type of covalent linkage that is desired to be formed.

Compositions of the present invention may be prepared using (1) a single type of lipid that is covalently linked to a glycosaminoglycan; (2) multiple types of lipids bound to the glycosaminoglycan, i.e., the compositions is prepared using multiple lipids in one or more reactions such that the glycosaminoglycan has multiple types of lipids attached to it; (3) a mixture of lipidated glycosaminoglycans, i.e., a mixture containing a glycosaminoglycan linked to a lipid A, the glycosaminoglycan linked to a lipid B, etc.; or (4) the use of more than one type of glycosaminoglycan.

Although a preferred aspect of the present invention relates to the use of hyaluronan, as exemplified below, analogous formulations may also be carried out using other glycosaminoglycans in a similar manner.

The compositions of the present invention may be used in a number of different applications, including the following when hyaluronan is used as the glycosaminoglycan:

(a) As a cosmetic, to rejuvenate epidermal and dermal skin cells by providing hyaluronan for the replenishment of the hyaluronan cell coating. Consequent to the presence of increased levels of hyaluronan in these layers is a rehydrating effect on the skin layers at a cellular level, and a "reverse aging" effect on the cells, which produces the appearance of younger looking skin. Through this rehydrating effect, the compositions may be used as a treatment to reduce the appearance of wrinkles, as well as to replenish the luminosity and dewiness characteristic of young skin.

(b) As a skin penetrant/retention system in which the modified hyaluronan is able penetrate the skin barrier when applied topically and which has a longer half-life within the skin than the resident hyaluronan, i.e., the compositions of the invention are degraded within the skin layers at a slower rather than naturally occurring hyaluronan.

(c) In the reduction of scarring, by promoting skin regrowth for patients with skin atrophy, e.g., atrophy due to immune problems or steroid use, as can be observed in cancer patients, the reduction of scarring following surgery, as well as general scar removal, e.g., general scarring, cellulite-associated scarring, stretchmarks, etc.

(d) In the treatment of actinic keratosis to reduce inflammation associated with actinic keratoses and to protect the damaged skin from further UVA/B damage. Modified hyaluronan compositions may also be formulated to deliver bioactive agents that reduce the proliferation of the keratinocyte layer that is affected by actinic keratoses.

(e) As a delivery system wherein a protein, polypeptide, or other similar-sized, biomacromolecule can be topically delivered through the skin barrier.

(f) As a drug delivery system wherein a pharmaceutically active ingredient is admixed with the lipidated hyaluronan compositions of the present invention to facilitate its dermal delivery. Such systems will provide a dual effect, delivering both the pharmaceutical ingredient and hyaluronan dermally; following dermal delivery of the drug, the hyaluronan portion of the system will then act as a rejuvenating agent for the dermal and epidermal cells, as described above. Particular therapeutic uses for the drug delivery systems of the present invention include:
  1. Targeting stromal cell deficiencies, for use in the treatment of inflammatory disease, cancer, skin regeneration/wound repair, chemical burns and thermal burns;
  2. The treatment of skin cancer;
  3. The treatment of skin conditions, such as acne, contact dermatitis, psoriasis and eczema;
  4. The treatment of disfiguring skin ailments through the reduction of scarring and the promotion of tissue regeneration; and
  5. The treatment of arthritis in joints, particularly the digits, for which injection is difficult.

The compositions of the invention may therefore be used in cosmetics, medicines (e.g., the treatment of burns and other conditions where hyaluronan is known to be beneficial), lubricants for mucous membranes, and as topical microenvironment drug delivery systems for pharmaceuticals. Cosmetic applications include reducing the appearance of wrinkles, enhancing the youthful appearance of skin, increasing collagen production within the skin, re-hydrating aged or dry skin, increasing the nourishment of skin, and treating the blotchiness associated with actinic keratoses. Applications for drug delivery include the topical administration of drugs, such as NSAIDs for the systemic or localized treatment of arthritis, chemotherapeutics for the systemic or localized treatment of skin cancers, and in applications as a substitute for patches or as a part of a patch (e.g., the composition of the present invention is embedded in a patch and applied to the skin, thereby allowing for a gradual absorption over time) for the administration of estrogen, nicotine, or other substances. Preferred non-cosmetic applications are those directed towards localized as opposed to systemic treatments, thereby minimizing systemic exposure of the drugs and consequently reducing the magnitude of side effects attributed to systemic exposure.

The compositions of the present invention may also be used in applications relating to tissue engineering by promoting tissue recovery by attracting stem cells (hyaluronan is known to attract stem cells), protecting resident stem cells from apoptosis (hyaluronan is known to protect stem cells) and reducing scarring (high hyaluronan levels in the skin reduces fibrotic repair). Use of the compositions of the invention in the reduction of scarring is also expected to aid in the recovery from paralysis since nerve cells cannot re-grow along their original tracks after, for example, a stroke or head injury because of fibrosis which essentially serves as a road block on the neural pathway. The reduction of fibrotic scarring will therefore lead to a decrease in the amount of nerve cells that are forced to wander around fibrotic tissue and are unable to regain their original path, thereby reducing or rendering temporary, these forms of paralysis.

Compositions using glycosaminoglycans other than hyaluronan, most particularly chondroitin sulfate, which is closely related to hyaluronan, may also be used in a number of different applications, including:

(a) As a cosmetic, to rejuvenate epidermal and dermal skin cells by providing a glycosaminoglycan capable of enhancing the ability of skin to retain water and/or bind to cell surfaces in place of hyaluronan.
(b) As a skin penetrant/retention system in which the glycosaminoglycan is able penetrate the skin barrier when applied topically.
(c) As a delivery system wherein a protein, polypeptide, or other similar-sized, large biomacromolecule can be topically delivered through the skin barrier.
(d) As a drug delivery system wherein a pharmaceutically active ingredient is admixed with the lipidated glycosaminoglycan compositions of the present invention to facilitate its dermal delivery.
   Particular therapeutic uses for the drug delivery systems of the present invention include:
     1. Targeting stromal cell deficiencies, for use in the treatment of inflammatory disease, cancer, skin regeneration/wound repair, chemical burns and thermal burns.
     2. Skin cancer
     3. Skin conditions, such as contact dermatitis, psoriasis and eczema
     4. Disfiguring skin ailments through the reduction of scarring and the promotion of tissue regeneration
     5. Arthritis in joints, particularly the digits, for which injection is difficult Uses of the glycosaminoglycan compositions involving the delivery of optionally added therapeutically-active substances are primarily directed towards the treatment of skin-related conditions. However, when the optionally added therapeutically-active substance is able to migrate through the epidermal and dermal layers to enter the systemic circulation following its delivery through the skin barrier, the compositions can be used more generally as a system to provide transdermal delivery.

Although the primary use of the compositions of the present invention are in topically applied formulations, applications of the present invention also include facilitating the oral uptake of glycosaminoglycans and drugs (wherein the modified hyaluronan acts as a drug delivery system), as well as facilitating the depositions of hyaluronan and hyaluronan drug-delivery systems following subcutaneous, intradermal, or other forms of injection. Further to their ability to penetrate the skin barrier, the compositions described herein may also be used to facilitate the penetration of mucous membranes and are may therefore be used to facilitate the delivery of the glycosaminoglycan compositions, as well as any optionally added therapeutic substances, by these additional pathways. Thus, the compositions of the present invention may also be used in formulations suitable for application to the buccal, esophageal, gastric, intestinal, nasal, olfactory, oral, bronchial, uterine, or penile mucosa. Additionally, the compositions of the present invention may be formulated to deliver the lipidated glycosaminoglycan and/or additional therapeutic agents to the inner eye, without requiring an injection, through topical application of an ointment, eyedrop or other suitable formulation.

The compositions of the present invention may be used in the preparation of formulations suitable for the desired method of application according to any method known to person skilled in the preparation of cosmetic and/or pharmaceutical products. Such methods are described, for example, in *Remington: The Science and Practice of Pharmacy or Cosmetic and Toiletry Formulations*, among numerous other texts. Preferred formulations include those that may be topically applied to the skin, such as creams, ointments, gels, lotions, or pastes. Additionally, the compositions of the present invention may also be used in patches typically used for the transdermal delivery of drugs, either on their own or as a delivery vehicle for a therapeutic substance, such as a drug or protein.

In addition to the preparation of formulations using standard methods and excipients, the compositions of the present invention may also be mixed with a standard, commercially available, cosmetic cream, and do not require the addition of any further or specialized penetration enhancers. The ability of the present compositions to penetrate the skin when administered with standard types of cosmetic creams also does not require the use of additional moisture barriers, such as wraps, impermeable plastic films or other types of barriers, to facilitate skin barrier penetration by preventing or reducing the ability of the skin to lose surface water.

Formulations containing the glycosaminoglycan compositions of the present invention may also include additional components such as anti-oxidants to assist in preventing the breakdown of hyaluronan and other glycosaminoglycans, whether naturally present or delivered as part of the compositions of the present invention. Formulations may also include vitamins, essential oils and other nutrients whose application is known to provide a beneficial effect to the health and/or appearance of skin. Additionally, formulations may also incorporate ingredients to reduce or prevent the damaging effects of UV radiation on the skin, such as those typically found in tanning lotions and sunscreens.

In order to aid in the understanding and preparation of the within invention, the following illustrative, non-limiting, examples are provided. In the examples described below, CD44−/− mice were obtained from Jackson Laboratories (Bar Harbor, Me.), RHAMM−/− mice were developed in-house according to the method described by Tolg et al.[19] using C57-BL6 wildtype mice obtained from Charles River Laboratories, and CD44−/−:RHAMM−/− mice were developed in-house according to the method described by Tolg et al.[20] Cells were also obtained using the methods described in Tolg et al.

Example 1. Preparation of a Non-Covalently Linked Hyaluronan-Phosphatidylethanolamine Conjugate (HA+PE)

An associated (non-covalently linked) hyaluronan-phosphatidylethanolamine complex (HA+PE) was prepared by mixing an aqueous hyaluronan solution (78.5 mL, 12 mg/mL; Baxyl®, Cogent Solutions Group, Lexington, Ky., USA) with soybean lecithin (78.5 mL; Soya Lecithin GT Non-GM IP containing 13% phosphatidylethanolamine; Imperial-Oel-Import) in isopropanol (10 mL) (to promote mixing) at room temperature for 30 minutes in a blender. The mixture was then incubated at 4° C. for 48 hr before being used in the preparation of a topical cream as described for the linked compositions of the invention in Example 4.

The lecithin used, in this example and the other examples described herein, contained 15% phosphatidylcholine, 13% phosphatidylethanolamine, 10% phosphatidylinositol, 19% other lipids, 5% carbohydrates, and 38% soybean oil. These phospholipids contain primarily $C_{14}$-$C_{22}$ fatty acids as the hydrophobic component, primarily stearic acid and palmitic acid, with smaller amounts of oleic acid, palmitoleic acid and myristic acid.

This non-covalently bonded material, which is outside of the scope of the present invention, was used in some of the following Examples for comparative purposes to demonstrate the effect of covalent bonding on the ability of the compositions of the invention to penetrate the skin barrier.

Experiments were also conducted using an analogous non-covalently linked conjugate prepared with ~350 kDa hyaluronan, however, no difference in the results were obtained when compared with the ~500 kDa conjugate described above.

Example 2. Preparation of a Linked Hyaluronan-Phosphatidylethanolamine Conjugate (HA-PE-1)

A covalently linked hyaluronan-phosphatidylethanolamine conjugate (HA-PE-1) was prepared by pre-mixing a hyaluronan solution (5 mL, 10 mg/mL de-ionized water, 50 mg; ~350 kDa (Life Core, MN, USA), ~$1.3 \times 10^{-4}$ mol —$CO_2H$ groups) with phosphatidylethanolamine (PE) (250 mg; Sigma-Aldrich®, cat no. 60648; 500 mg assayed at ~50%) with rapid stirring via hand blender. Prior to addition of the phosphatidylethanolamine to the hyaluronan, it was first dissolved in chloroform (0.5 mL), which was then evaporated off, replaced with isopropanol (0.5 mL), and brought into suspension with a hand vibrating probe. 1-ethyl-3-(3-dimethylaminopropyl)carbodiimide (EDC) (1.2 mg, $7.7 \times 10^{-6}$ mol; 10 µL of a freshly prepared stock solution containing 120 mg EDC dissolved in de-ionized water (1 mL)) was added and thoroughly mixed for 30 minutes, then left at room temperature for 2 hours.

HA-PE-1 was used in the cellular assays (Example 5, Example 6, Example 7, and Example 8).

Based upon the amount of EDC used as the linking reagent, and the expectation that a freshly prepared solution of EDC (as used above) will allow for a near quantitative linking, the expected degree of linking for Example 2 is that ~6% (upper maximum) of the disaccharide units of the hyaluronan will have been modified with covalently-linked phosphatidylethanolamine groups. It is expected that linking efficiency would be decreased in the event that the EDC were previously exposed to water.

Example 3. Preparation of a Linked Hyaluronan-Phosphatidylethanolamine Conjugate (HA-PE-2)

In addition to the use of pure phosphatidylethanolamine, such as in Example 2, mixtures of lipids containing phosphatidyl ethanolamine may also be used. For example, liquid soy lecithin (Soya Lecithin GT Non-GM IP, Imperial-Oel-Import) contains approximately 15% phosphatidylcholines, 13% phosphatidylethanolamines, 10% phosphatidylinositols, 19% other phospholipids and lipids, 5% carbohydrates, and 38% soybean oil. This is approximately 330 mg phosphatidylethanolamines (the only lipid expected to react in large amounts using EDC as a linking agent) per tablespoon (14.79 mL).

Unrefined liquid soy lecithin (78.5 mL; Soya Lecithin GT Non-GM IP, Imperial-Oel-Import) was mixed with hyaluronan (78.5 mL, 12 mg/mL, 942 mg, ~$2.5 \times 10^{-3}$ mol —$CO_2H$ groups; 500-2,500 kDa, polydisperse Baxyl HA, Cogent Solutions Group, Lexington, Ky.) and isopropanol (10 mL) with rapid stirring via hand blender for 10-15 minutes at room temperature. 1-ethyl-3-(3-dimethylaminopropyl)carbodiimide (EDC) (22 mg, $1.4 \times 10^{-4}$ mol; 100 µL of a freshly prepared stock solution of 220 mg EDC in 1 mL ice cold de-ionized water) was added, mixed for an additional 10-15 minutes, and then allowed to stand at room temperature for 2 hours. Alternatively, when the scale of the reactions permits accurate weighing of the EDC, compositions may also be prepared where the EDC is added directly, i.e., without the preparation of a stock solution. The obtained HA-PE-2 was stored at 4° C. and used without further purification in the preparation of cosmetic formulations (see Example 4) for use in the mouse (see Example 9, Example 10, Example 11, and Example 13) and human (see Example 14, Example 15, Example 16, Example 17, Example 18, and Example 19) studies.

Based upon the amount of EDC used as the linking reagent, and the expectation that a freshly prepared solution of EDC (as used above) will allow for a near quantitative linking, the expected degree of linking for Example 3 is that ~5.5% (upper maximum) of the disaccharide units of the hyaluronan will have been modified with covalently-linked phosphatidylethanolamine groups. It is expected that linking efficiency would be decreased in the event that the EDC were previously exposed to water.

Example 4. Preparation of Topical Creams

Topical creams of the modified hyaluronan prepared in Example 2 or Example 3 may be prepared by suitable procedures commonly used in the art for the preparation of cosmetic and medicinal creams for topical application. The preparation described below should be viewed as a non-limiting example.

The gel, HA-PE-2, obtained in Example 3 was mixed at a 1:1 (v/v) ratio with a commercially available base cream (NIVEA Creme; ingredients: water, mineral oil, microcrystalline wax, glycerin, lanolin alcohol, paraffin, panthenol, decyl oleate, octyldodecanol, aluminum stearate, citric acid, magnesium sulfate, magnesium stearate, methylchloroisothiazolinone, fragrance) in a blender and stored at 4° C. until use. This storage temperature was used as a precautionary measure owing to the lack of additional additives to the creams, e.g., antimicrobials to prevent to potential degradation of hyaluronan, and should not be seen as a limitation on the formulations themselves.

Use of alternate base creams, e.g., OIL OF OLAY® (OLAY® Classic Moisturizing Crème; ingredients: water, glycerin, cetyl alcohol, petrolatum, cyclopenasiloxane, stearyl alcohol, isopropyl palmitate, dimethicone, carbomer, PEG-100 stearate, stearic acid, sodium hydroxide, DMDM hydantoin, iodopropynl butylcarbamate, EDTA, fragrance, titanium dioxide, Red 4) or L'ORÉAL® (Dermo-expertise wrinkle defense anti-aging cream; ingredients: water, cyclopentasiloxane, hydrogenated polyisobutene, cetyl alcohol, glycerin, glycerylstearate, PEG-40 stearate, myristylmyristate, ethylhexylpalmitate, butyro-spermum parkii butter, sorbitan tristearate, glycine soya protein, methylparaben, dizolidinylurea, tocopherylacetate, acrylates copolymer, propylparaben, limonene, disodium EDTA, hydroxycitronellal, linalool, benzyl alcohol, benzyl benzoate, butylphenylmethylpropional, guanosine, alpha-isomethylionone, citral, eugenol, chlorphenesin, sodium dehydroacetate, fragrance, FIL K29371/2), in the following examples did not lead to any differences in the bioactivity or effect of the modified hyaluronan.

In addition to the use of the above, or other, commercially available creams, suitable formulations for topical use may also be prepared using commonly known methods. In addition to the modified glycosaminoglycan, other components, whether for fragrance or any other cosmetic, dermatologic or medical property, may be also be added to the preparation.

Example 5. Modified Hyaluronan (HA-PE-1) Forms Increased Cell Coats on Human Dermal Fibroblasts The suitability of the present compositions was assessed by determining its ability to encase/surround cultured dermal fibroblasts grown from a punch biopsy of human skin. Punch biopsies were placed in a sterile tissue culture dish (35×10 mm, tissue culture dish) and cut with small (e.g., 19 G) sterile needles into small fragments. The fragments were allowed to dry briefly (e.g., no more than 10 minutes) to the bottom of the tissue culture dish to promote adherence of the tissue fragments. Dulbecco's modified Eagles Medium (DMEM), supplements with 10% fetal calf serum (FCS) was then gently added and the culture is then placed in a humidified 37° C. incubator supplemented with 5% $CO_2$ for approximately one week. The fibroblasts that have grown out of the explants are then removed from the tissue culture plate in sterile 0.025% trypsin/EDTA mixture and gently spun at 1.1×g for 3 minutes, following which the trypsin is removed and the cells are plated at 1:5 dilution in fresh, sterile tissue culture plates at a density of 50,000/well (24 well plates) onto sterilized glass coverslips in 1 mL DMEM supplemented with 10% fetal calf serum in a humidified 5% $CO_2$ atmosphere. After 18 hours, cells were exposed to either a hyaluronan solution (500 µg/mL, 350 kDa) or modified hyaluronan (HA-PE-1) (25 µg/mL) for 1 hour. 30-40 nm fluorescent yellow polystyrene nanospheres (Corpuscular Inc., Cold Spring, NY) were added to the wells and allowed to settle onto the adherent cells at 37° C. for 30 minutes. Cultures were then fixed in freshly prepared paraformaldehyde and mounted on a glass slide that contained a hollow well. The cells were photographed (see FIG. 1) on a Nikon Eclipse TE300 inverted microscope equipped with Hoffman Optics and epifluorescence. In another method for detecting Hyaluronan coats, used below for in Example 7, paraformaldehyde-fixed sheep mature erythrocytes were added to the wells and allowed to settle as above. Cell coats revealed by this methods were photographed with the above Nikon inverted microscope using Hoffman optics (see FIG. 5).

In the images shown in FIG. 1, the hyaluronan cell coat is observed as a dark space since small fluorescent beads are excluded by the coat as denoted by the arrow within the image. Cells without coats cannot be detected by this assay as they are entirely covered by the fluorescent beads. As seen in FIG. 1, the addition of hyaluronan alone (image 12) to the culture medium had little additional effect on the size of the hyaluronan coats as compared to the PBS control (image 11). The addition of HA-PE-1, to the culture medium (image 13) resulted in a clearly observable increase in the hyaluronan coat as detected by the exclusion of fluorescent beads around the cells, creating a halo effect.

Example 6. Effect of Modified Hyaluronan (HA-PE-1) on the Percent of Cells with Hyaluronan Coats and Hyaluronan Coat Size Modified hyaluronan (HA-PE-1), prepared according to Example 2, or hyaluronan alone (350 kDA; 10 mg/mL stock solution in saline) was added to senescent human fibroblasts in increasing concentrations (0-100 µg/mL). The percentage of cells that exhibited hyaluronan coats (see FIG. 2) increased with the concentration of HA-PE-1 in contrast to the addition of hyaluronan alone. The use of unmodified hyaluronan alone resulted in fewer cells with hyaluronan coats and the percentage of cells with coats reached a plateau at a concentration of 10 µg/mL. In contrast, the addition of modified hyaluronan (HA-PE-1) resulted in a dose dependent increase in the percentage of cells with hyaluronan coats so that the percentage of cells with coats was significantly greater in the presence of 100 µg/mL HA-PE-1 than with 50 µg/mL HA-PE-1 (Student's "t" test, p<0.01). At all concentrations, the addition of HA-PE-1 resulted in significantly more cells with hyaluronan coats than the addition of unmodified hyaluronan alone (Student's "t" test, p<0.0001).

Figure 3:
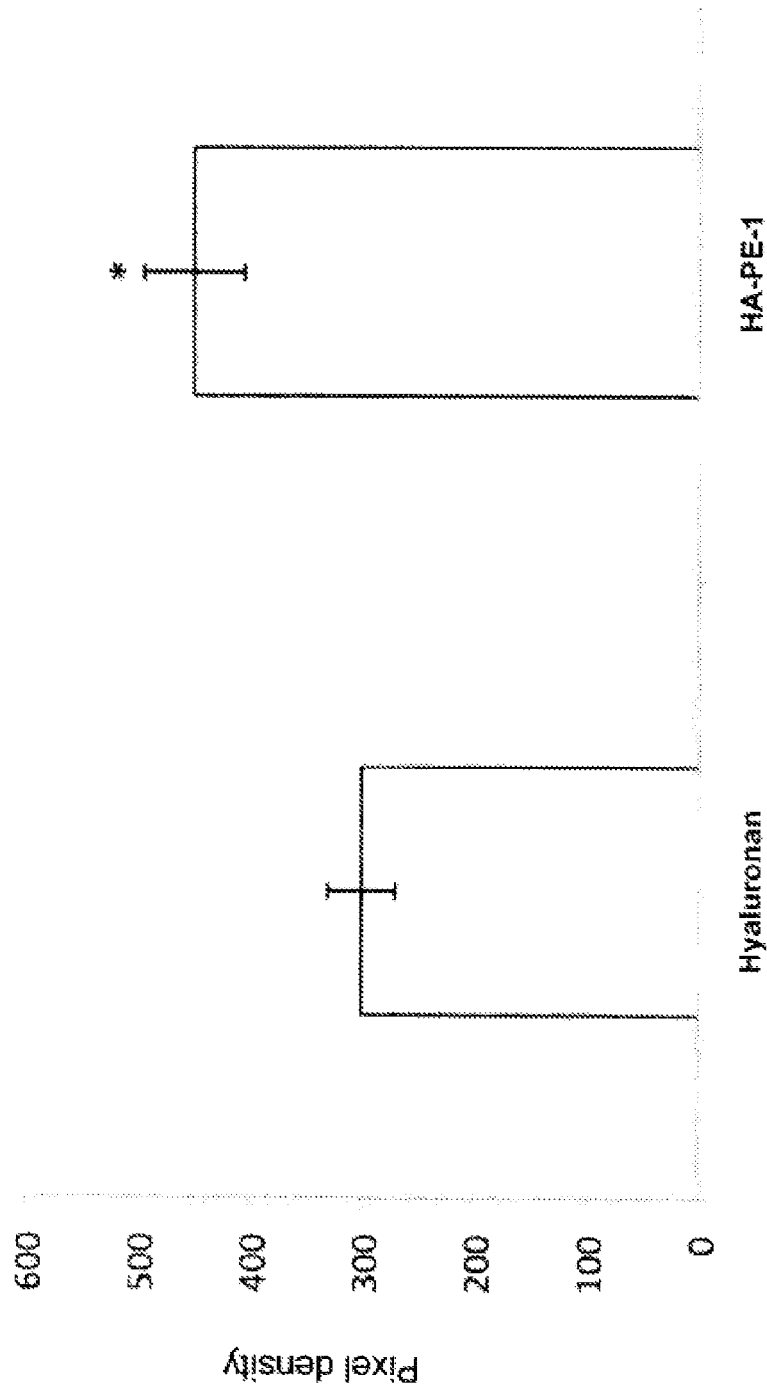

The effect of the addition of modified hyaluronan (HA-PE-1; 50 µg/mL) vs. hyaluronan alone (50 µg/mL) on the cell coat area of the cells was quantified using image analysis (Elements 3.1, Nikon). At these concentrations the application of the modified hyaluronan (HA-PE-1) significantly increased the average hyaluronan coat size/cell when compared to HA alone (Student's "t" test, p<0.05) (see FIG. 3). Values are means and S.E.M. for 10 samples.

Example 7. Ability of Modified Hyaluronan (HA-PE-1) to Coat Mouse Embryo Fibroblasts without Hyaluronan Receptors Hyaluronan normally binds to cells via interactions with hyaluronan receptors such as CD44, RHAMM, LYVE-1 and Toll-like receptors 2,4. Mouse embryonic fibroblasts selectively express CD44 and RHAMM, the two receptors responsible for the ability of these cells to bind to hyaluronan and produce a hyaluronan coat.

Figure 4:
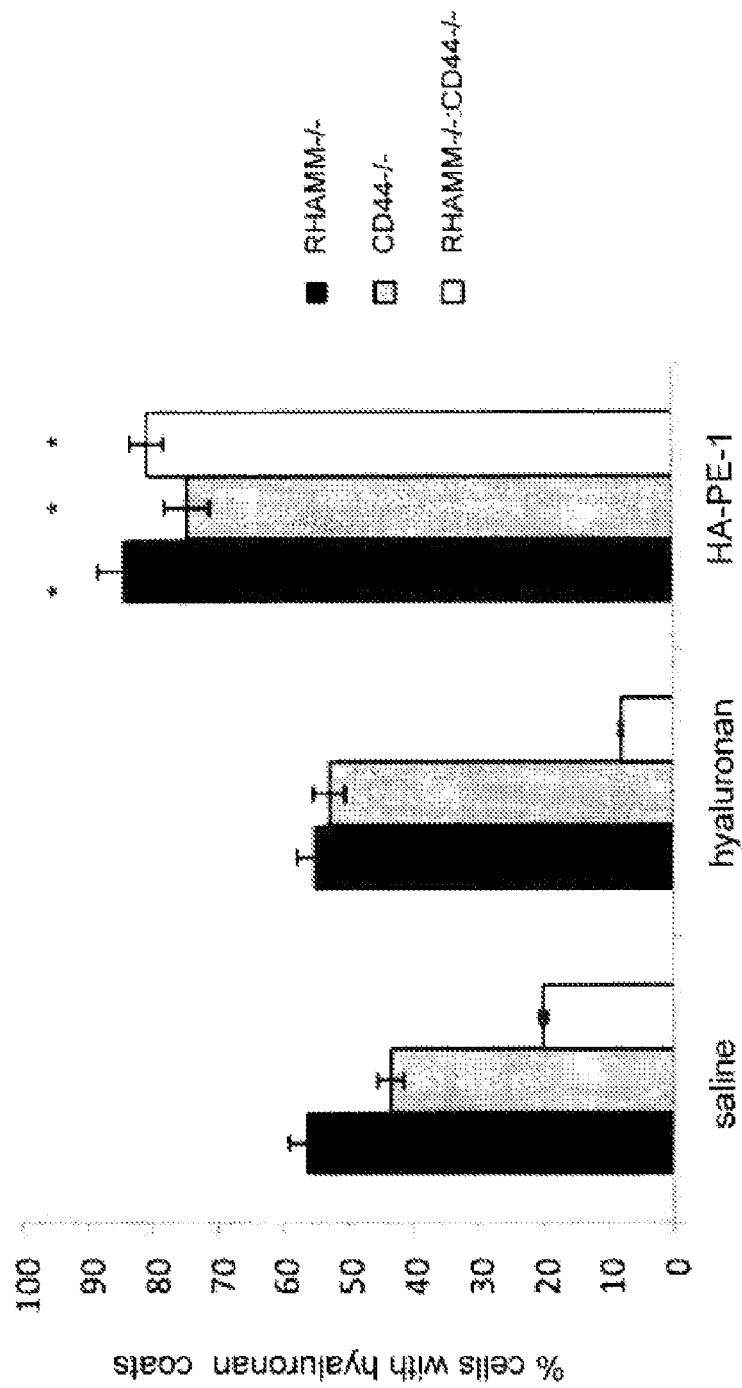

Mouse embryonic fibroblasts were isolated from CD44-/-, RHAMM-/- and CD44-/-:RHAMM-/- embryos (Day 14), i.e., embryos without CD44, RHAMM, and CD44 and RHAMM hyaluronan receptors, respectively, and immortalized clones were obtained by limiting dilution. Modified hyaluronan prepared according to Example 2 (HA-PE-1) or hyaluronan alone was added to the culture medium as described in Example 5. Unlike Example 5, which visualized cell coats using fluorescent nanospheres, hyaluronan cell coats were visualized using fixed sheep erythrocytes, which acts as particles and which are excluded from the bottom of the dish wherever cells form a hyaluronan coat, that are observed using Hoffman optics rather than epifluorescence. Cells that do not form coats are buried under the erythrocytes and are not visible under the detection conditions. Areas that lack erythrocytes represent cells containing mouse embryonic fibroblasts containing hyaluronan coats. Values obtained for the graph in FIG. 4 are the mean and S.E.M for 10 samples of each treatment and genotype.

Figure 5:
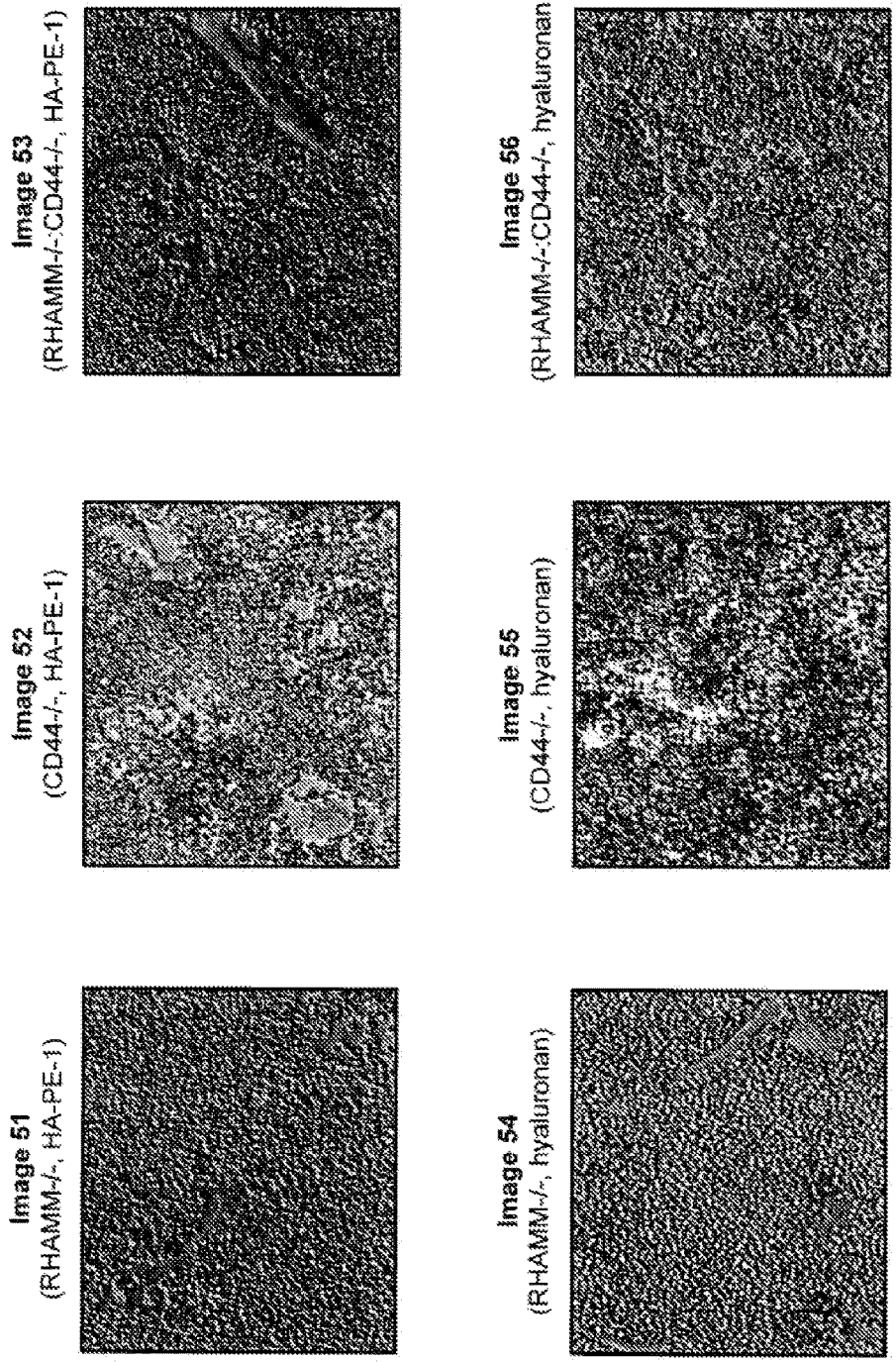

As observed in FIG. 5, the addition of modified hyaluronan (HA-PE-1) (images 51 (RHAMM-/- cells), 52 (CD44-/- cells), 53 (RHAMM-/-:CD44-/- cells)) increased both the size of the hyaluronan coats and numbers of cells containing hyaluronan coats when compared with cells treated with hyaluronan alone (images 54 (RHAMM-/- cells), 55 (CD44-/- cells), 56 (RHAMM-/-: CD44-/- cells)). The ability of the modified hyaluronan (HA-PE-1) of the present invention does not appear to be dependent upon the expression of hyaluronan receptors common to fibroblasts since loss of either one or both of the CD44 or RHAMM receptors, the two most prevalent hyaluronan receptors, does not significantly influence the number of cells that have hyaluronan coats (see images 51 (RHAMM-/- cells), 52 (CD44-/- cells), 53 (RHAMM-/-: CD44-/- cells), and FIG. 4). Furthermore, the application of the modified hyaluronan (HA-PE-1) significantly increased (Student's "t" test, p<0.001) the percentage of cells with hyaluronan coats in all genotypes versus the addition of saline (images not shown, results included in FIG. 4) or hyaluronan (500 µg/mL; 350 kDa).

The above in vitro testing (Example 5, Example 6 and Example 7) indicates that covalently-linked hyaluronan phospholipid derivatives (e.g., HA-PE-1) are better able to provide cell coats than unmodified hyaluronan. The ability of HA-PE-1 to bind to mouse embryonic fibroblasts that do not express hyaluronan receptors suggests that the modified hyaluronan of the present invention do not require an interaction with a hyaluronan receptor to associate with the cell membrane, and likely directly inserts its lipid tail into the phospholipid layers of the cell membrane. This does not preclude an association of the modified hyaluronan with hyaluronan receptors if they are expressed by the cells. The large cell coats observed in cells that lack CD44 and RHAMM expression further suggest that the modified hyaluronan-cell interaction is stable.

Example 8. Enhancement of SKL-Catalase Function with Modified Hyaluronan Compositions SKL-catalase is a genetically modified enzyme that is more effective in reducing reactive oxygen species (ROS) inside cells than the unmodified endogenous catalase. Catalases are necessary to reduce the toxicity resulting from ROS that contribute to aging. One function of SKL-catalase is to reduce the fragmentation of hyaluronan resulting from ROS. Through the use of the compositions of the present invention, it has been found that the phosphatidylethanolamine-hyaluronan conjugates described herein were able to enhance the function of SKL-catalase.

Catalase recombinant protein (human erythrocyte, 10 µg/mL, Sigma) was derivatized with SKL to permit entry into cells.[21] The resulting SKL-catalase was mixed with HA-PE-1 and added to a culture of senescent human fibroblasts. The resulting images (see FIG. 6) indicate that for cells treated with the hyaluronan-phosphatidylethanolamine conjugate of Example 2 (HA-PE-1) and SKL-catalase (image 63), cell coats where larger than those formed when either SKL-catalase (image 61) or HA-PE-1 (image 62) were added alone. These results indicate that the hyaluronan compositions of the present invention enhance the effects of SKL-catalase on ROS production, based upon the observation of increased cell coat size. These results suggest that the hyaluronan derivatives of the present invention are able to capture a variety of proteins and retain them at the cell surface, which is consistent with the compositions of the present invention acting via a molecular net-type mechanism.

The following examples (Example 9, Example 10, Example 11, and Example 12) demonstrate that the compositions of the present invention are able to cross the skin barrier in mice following topical administration. It is believed that this model is sufficient to reasonably predict the ability of the compositions of the invention to similarly pass through the skin barrier of humans.

Example 9. Topical Application of HA-PE-2 to Mice

HA-PE-2 (prepared as described in Example 3) was formulated (1:1 v/v) with NIVEA Creme base cream as described in Example 4. The cream was then applied (0.18 g HA-PE-2/application) to the shaved backs of 9-month old female mice (BL6 strain, 40×30 mm area of shaved skin) once daily for 4 days. The application of base cream mixed with soya lecithin (1:1) served as a control. On the fifth day, mice were euthanized and the treated skin was harvested with an 8 mm biopsy punch and fixed in freshly prepared 4% paraformaldehyde/phosphate buffered saline. Fixed tissues were processed in paraffin, sectioned and stained for hyaluronan using an Echelon® kit (Hyaluronan ELISA test kit, Echelon). Keratinocytes in skin to which HA-PE-2 was applied stained more darkly for hyaluronan than those in skin to which cream only was applied (p<0.00001, Student's "t" test) and had a thicker epidermal layer than in control mice. The density of Hyaluronan staining was quantified using image analysis (Elements 3.1, Nikon). FIG. 7 provides images of the skin sections for treated (images 71 and 72) and control (images 73 and 74). The increase in hyaluronan presence in the keratinocytes is demonstrated by calculating the pixel density of the images, as shown in the accompanying graph in FIG. 8. The underlying dermal layer of mice contained high levels hyaluronan in both HA-PE treated and control animals (see FIG. 8). These results indicate that the modified hyaluronan of the present invention penetrates the skin barrier and binds within at least the dermal keratinocyte layer. Values are the means and S.E.M. of four mice for each treatment.

Example 10. Comparison of the Ability of HA-PE-2 and Hyaluronan to Penetrate the Skin Barrier of Mice HA-PE-2, prepared as described in Example 3, hyaluronan mixed with, but not covalently linked to, lipids in the lecithins present in Example 3 (see Example 1), and hyaluronan alone (no additional phospholipid), were each formulated with a NIVEA Creme cosmetic base cream (1:1, v/v) as described in Example 4. The creams were then applied to the shaved backs (0.18 g HA-PE-2/application, 40×30 mm shaved area) of 9-month old female BL6 wild-type mice once daily for 4 days. After this time, one group of animals was euthanized and processed according to the procedure described in Example 9. A second group of animals were left without further treatment for an additional 2 days and euthanized/processed as described in Example 9 on day 7. The images in FIG. 9 and accompanying graph (FIG. 10), which quantifies the amounts of hyaluronan that was able to penetrate the skin barrier, indicate significantly stronger staining for hyaluronan for mice treated with HA-PE-2 (image 91) than with a mixture of hyaluronan and phosphatidylethanolamine (image 92), or hyaluronan alone (image 93), both of which showed negligible amounts of hyaluronan penetrating the skin barrier (Student's "t" test, p<0.000001) in comparison to HA-PE-2. Following cessation of treatment, the amount of hyaluronan present in the keratinocytes gradually decreases, as illustrated by the reduction of hyaluronan staining in the mice treated with HA-PE-2 (see image 94 and FIG. 10). As expected, the amounts of hyaluronan staining in the other mice (see images 95 and 96, and FIG. 10) remained negligible.

These results demonstrate the enhanced ability of the modified hyaluronan compositions of the present invention to penetrate the skin barrier as compared to the use of a mixture of hyaluronan and lipids present in soya lecithin (including phosphatidyl ethanolamine), or with hyaluronan alone, in a cosmetic base cream. More importantly, the modified hyaluronan that is able to penetrate the skin barrier is retained within the keratinocyte layer, in accordance with the increased ability of the modified hyaluronan compositions of present invention to associate with cells as demonstrated in Example 5. As mentioned above, Brown et al.[14] has previously reported the passage of similarly sized hyaluronan fragments through the skin barrier, however, this hyaluronan readily enters the systemic circulation and is eliminated from the body. Similar findings have been reported by Kaya et al.,[5] who similarly showed that 50-400 kDa hyaluronan can cross the epidermis and also increase keratinocyte layer thickness, but that the applied hyaluronan (using tagged hyaluronan) is not retained within the epidermis, is rapidly lost from the dermis, and requires CD44 expression in the cells for functional effects. The present results further confirm that if skin penetration by unmodified hyaluronan does occur, it is not retained within the skin to an appreciable extent, and is therefore unable to act in a manner that would replenish hyaluronan levels within the skin.

Since the amount of endogenous hyaluronan in skin can vary with location, internal controls were designed to evaluate hyaluronan staining of treated and control skin were developed to confirm the difference between the treated vs. untreated skin area. HA-PE-2 and control creams (hyaluronan only) were applied to the shaved backs of mice as previously described. Areas of treatment were marked (hair in the adjacent untreated margins was removed with Nair™ and the punch aligned to include the treated and untreated region; tissue punches were orientated in small tissue baskets to keep the tissue in the correct orientation throughout processing and marked with a histology marker pen) and tissue was harvested/processed as previously described (Example 9). The resulting samples indicate (see FIG. 11; the application edge is indicated with an arrow and the application area with a broken line) that when hyaluronan alone was applied, a distinct margin of staining was not observed (image 111), which confirmed that very little if any penetration/retention of the applied hyaluronan occurred in the application area. In contrast, a distinct boundary of staining, which was significantly higher in the treated vs. untreated area of skin (Student's "t" test, p<0.000001), was observed at the edge of the HA-PE-2 application (image 112). As quantified by the accompanying graph in FIG. 12, these results confirm that the modified hyaluronan compositions of the present invention penetrates and accumulates within the epidermis at the site of application and suggests that this remains localized to the original area of application.

Example 11. Replacement of Hyaluronan Cell Coats Using HA-PE-2 in Mice without Hyaluronan Receptors A cream containing HA-PE-2 (0.18 g HA-PE-2, prepared as previously described) was applied daily (40×30 mm shaved patch) to the shaved backs of 9 month old female RHAMM−/− mice (mice that express the CD44 hyaluronan receptor but not the RHAMM hyaluronan receptor) for 4 days. Animals were euthanized on day 5 after treatment and treated skin was harvested as described in Example 9. Mouse skin to which base cream alone was applied served as a control. As shown in FIG. 13, images 131 and 132, and the accompanying graph, HA-PE-2 treated epidermis (image 131) retained hyaluronan to a significantly greater extent than control skin (image 132), which showed negligible hyaluronan levels (Student's "t" test, p<0.000001). Values represent the mean and SEM for 4 mice.

HA-PE-2 was also applied to the shaved backs of 9 month old female CD44−/−:RHAMM−/− mice (neither the CD44 nor the RHAMM hyaluronan receptors are expressed; developed as described by Tolg et al.[22]) as described above and using a similar control. As seen in FIG. 14, images 141 and 142, and the accompanying graph, treated skin (image 141)

accumulated significantly more hyaluronan in the epidermal layer than control skin (image 142). Values represent the Mean and S.E.M. for 4 mice. This indicates that the modified hyaluronan compositions of the present invention do not require hyaluronan receptors (CD44 and RHAMM, which are the primary are receptors in skin) in order to associate with keratinocytes. These results, together with the known ability of phosphatidylethanolamine to insert into cell membranes indicate that the modified hyaluronan directly intercalates into the cell membrane without the aid of hyaluronan receptors. A comparison of the staining for endogenous hyaluronan and HA-PE-2 in the epidermal layer of RHAMM−/− (CD44+) mice (FIG. 13) with that of hyaluronan receptor negative (CD44−/−:RHAMM−/−) mice (FIG. 14) shows that staining for both endogenous hyaluronan (images 132 and 142) and following HA-PE-2 (images 131 and 141) treated epidermis is greater when CD44 is expressed than when both hyaluronan receptors are absent. These results suggest that both endogenous and hyaluronan-phosphatidylethanolamine conjugate (HA-PE-2) coats are stabilized by the presence of CD44 receptors, consistent with the known involvement of CD44 receptors in promoting endogenous hyaluronan coats in cultured cells.

Example 12. Comparison of Compositions of the Invention with Particulate Phosphatidylethanolamine-Hyaluronan Materials Described in WO 2003/015755

Particulate (nano- and microsphere) phosphatidylethanolamine-hyaluronan conjugates were prepared using the methodology described by Margalit in WO 2003/015755. A beaker was coated with 2 mL soya lecithin. Hyaluronan (2 mL, 12 mg/mL, $6.3 \times 10^{-5}$ mol —$CO_2H$ groups; 500-2,500 kDa polydisperse, Baxyl™, Cogent Solutions Group) was activated by lowering the pH to 4.5 and then adding EDC (2.5 mg, $1.6 \times 10^{-5}$ mol; from a freshly prepared stock solution), following which the activated hyaluronan was added to the lecithin-coated beaked followed by the addition of de-ionized water (1 mL) and adjustment of the pH to 8.6 with NaOH. The resulting mixture was incubated at 37° C. and shaken end over end overnight, after which the pH was adjusted to 7.2 and the mixture was sonicated for 10 minutes and centrifuged 2 times at a g force of $1.2 \times 10^5$ at 40° C. for 40 minutes to isolate the particulate material. Based upon the amount of freshly prepared EDC stock solution used, the expected theoretical maximum amount of linkage between the phosphatidylethanolamine and hyaluronan is estimated to be ~25%. The obtained material was added directly to glass slides and mixed with a cream base in the same manner as described for the present invention, following which it was applied to a glass slide.

The particulate samples, prepared using methodology previously described in the patent literature by Margalit, were compared with the compositions of the present invention. Hyaluronan-phosphatidylethanolamine conjugates, as described in Example 3 (HA-PE-2) were applied directly to a glass slide as prepared, and as a 1:1 mixture with a base cream as described in Example 4 (NIVEA Creme base cream) that was also applied to a glass slide.

All samples were covered with a coverslip and examined on a Nikon TE300 inverted microscope with Hoffman optics at 40×, with the images obtained being reproduced in FIG. 15. The vesicular or particulate nature of the particulate compositions prepared according to the methodology described by Margalit in WO 2003/015755 is clearly observed in images 153 (direct application) and 154 (cream preparation). However, the compositions of the present invention, as shown in images 151 and 152, fail to indicate the presence of similarly self-assembled materials.

A primary application of the present invention is as a vehicle for the delivery of hyaluronan to the epidermal and dermal layers of the skin, where it can serve to replenish areas of the skin that are deficient in the amount of hyaluronan present.

Following the preparation of the modified hyaluronan of the present invention, e.g., as described in Example 2 or Example 3, formulations may be prepared following processes and procedures known in the art, or through the use of commercial or other stock cosmetic creams as described in Example 4. In addition to the inclusion of the modified hyaluronan compositions of the present invention, formulations may also include other cosmetically active ingredients, such as those commonly found within commercial skin creams, including those known to provide assistance in rejuvenating the appearance of skin, e.g., vitamins, amino acids, coenzymes, β-glucans, polynucleotides, radical scavengers, growth factors, estrogens, and adipogenic factors, among others. Formulations may also include the addition of hyaluronidase inhibitors,[23] to reduce the rate of hyaluronan decompositions in the skin, or the addition of RHAMM inhibitors, which have been demonstrated to induce the generation of subcutaneous fat cells lost through aging processes.[22] Additionally, formulations may include pharmaceutically active ingredients, particularly active ingredients used to treat skin conditions, such as skin cancer, contact dermatitis, psoriasis, and eczema. As a result, the present invention provides a method to allow for a localized, topical, treatment for the delivery of pharmaceuticals rather than through systemic administration via oral or intravenous dosage forms or the requirement of injections to provide subcutaneous or intradermal administration.

In a further aspect of the invention, the derivatized glycosaminoglycan may also be used to transport proteins across the skin barrier. This transport ability is unexpected and believed to be sufficient to allow for the targeted delivery of small (700 Da) to large (400-500 kDa) proteins to at least the dermal and epidermal layers of the skin, as well as the underlying muscle. Thus, the compositions of the present invention may be useful in additionally providing a cosmetically important large proteins, such as Botox™, through a topical application, thereby eliminating the need for a series of injections. The ability of the present invention to dermally deliver proteins, also allows for the topical administration of therapeutic proteins, such as hyaluronidase and RHAMM inhibitors; interferons or anti-inflammatory proteins/cytokines; anti-skin cancer therapies, such as antibodies, recombinant proteins, protein fragments, and peptides; and vaccinations using peptides/proteins, thereby providing treatment to a localized area rather than through systemic or injected routes of administration, which is expected to reduce or eliminate the occurrence of side effects generally associated with systemic treatments. As well, the compositions of the invention could be used to deliver enzymes, such as hyaluronan synthase, to aid in the production hyaluronan within the skin. Additionally, other large molecules, such as DNA, RNA or cDNA, could be administered topically by this method.

Although the use of lipidated glycosaminoglycans have previously been described for use as delivery vehicles for proteins (e.g., Margarlit and Peer in WO 03/015755), these examples involve the entrapment of the protein within a self-assembled particulate structure. Based upon the action of the compositions of the present invention, and the results of the experimentation that have been conducted to date, as described in the preceding examples, it is believed that, unlike the prior descriptions of protein delivery known in the art, the compositions described herein do not rely upon an encapsulation mechanism since the present compositions do not appear to self-assemble in an organized fashion. Rather, it is believed that the compositions of the present invention are able to facilitate the delivery of proteins through the skin barrier via an unorganized tangling mechanism of the lipidated glycosaminoglycan around and within the protein. The ability of the present invention to provide dermal protein delivery is described in the following example.

Example 13. Transport of RHAMM Proteins Through the Skin Barrier Using Modified Glycosaminoglycans (HA-PE-2)

Murine GST-RHAMM (35 µg from a 1 mg/mL stock solution), an 84 kDa tagged protein, or murine GST (26 kDa) alone (35 µg from a 3 mg/mL stock solution) was mixed with HA-PE-2 (0.18 g) in a NIVEA Creme base cream in the same manner as described in Example 4. A preparation of hyaluronan in a NIVEA Creme base cream with the proteins was used as a control. 0.18 g of treatment (containing 35 µg protein) and control cream was applied to a 40×30 mm area of shaved skin on the backs of 9-month old female BL6 wildtype mice every day for 5 days, with mice being euthanized on day 6. Skin patches were harvested using an 8 mm biopsy punch and the tissue was fixed in freshly prepared 4% paraformaldehyde then paraffin processed. 8 µm sections were cut perpendicular to the biopsied tissue and sections were stained for GST using anti-GST antibodies prepared in goat. Bound antibody was visualized using biotinylated goat anti-rabbit antibody, streptavidin-horse radish peroxidase and Dab, which produces a brown stain when anti-GST antibody is bound to the slide. GST rather than RHAMM antibodies were also used to detect GST-RHAMM since skin does not normally express GST. Visualization of the samples (see FIG. 16) indicates that GST-RHAMM was carried through the skin barrier of mice and to the underlying muscle layer when delivered with the composition of the present invention (image 161), while GST-RHAMM was barely detected in the keratinocyte layer in the control sample containing unmodified hyaluronan (image 163). The relative amounts of GST-RHAMM reaching both the keratinocyte layer and underlying muscle are quantified in the accompanying graph in FIG. 17 which represents mean values for 5 mice. Similar results were observed for the smaller GST protein (26 kDa) (see FIG. 16, images 162, delivered with HA-PE-2, and 164, delivered with unmodified hyaluronan).

Previously, transdermal delivery of proteins was considered to be limited to less than 10,000 Da with the use of penetration enhancers. The long list of methods that have been devised to attempt to promote topical and transdermal delivery of proteins and peptides, such as liposomes, enhancers such as alcohols, DMSO, monoterpenes and fatty acid esters, physical modification of pro-drugs and use of physical methods for increasing the permeation of skin (e.g., ethanol-water hydration, stripping of outer keratinocyte layer) and chemical delivery means (e.g., electrical and thermal treatments of skin) attests both to the difficulties of transdermal delivery and the need for an efficient and effect delivery method. Such methods are described by, for example, Sugino et al.,[24] Skountzou and Kang,[25] and Antosova, at al.,[17] among others. Therefore, the method of protein delivery using compositions of the present invention represents a significant improvement in the ability to deliver proteins through the skin barrier. While any glycosaminoglycan may be modified according to the present invention in order to act as a carrier for proteins and/or other pharmaceutically or cosmetically desirable materials through the skin barrier, the use of hyaluronan as the glycosaminoglycan is generally preferred owing to its natural presence in the skin, and ready availability in high molecular weights.

In addition to their use in the delivery of proteins across the skin barrier, the glycosaminoglycan compositions of the present invention may also be used to deliver other biomacromolecules across the skin barrier. Other biomacromolecules would include, for example polypeptides (including enzymes), proteoglycans, carbohydrates/polysaccharides, nucleic acid chains, protein and peptide therapeutics, anti-sense therapeutics, bioactive artificial polymers and bioactive lipid polymers.

Although the protein transported across the skin barrier in Example 13 was 84 kDA, this is not believed to be a limiting size (RHAMM is known to dimerize and trimerize, while GST, which also self-associates, promotes the aggregation of RHAMM with itself; thus the actual size of the protein transported may be up to 255 kDa (a GST-RHAMM trimer)), and was chosen owing to its availability and similarity in size to Botox™ (150 kDa), a protein of interest in the cosmetic applications of the present invention. Rather than size, a main limiting factor in the selection of suitable biomacromolecules is expected to be their ability to become entangled within the molecular nets that are believed to be formed by the glycosaminoglycan compositions of the invention. Thus, with increasing size, substantially linear biomacromolecules, e.g., collagen fragments, are expected to be less prone to transport to a greater extent that similarly sized non-linear biomacromolecules, e.g., proteins.

The following examples, which are not intended to be limiting upon the scope of the invention, demonstrate the effectiveness of the modified hyaluronan described above (HA-PE-2) when used in the topical treatment of human subjects encountering a variety of skin-related conditions.

Example 14. Treatment of Wrinkles

Skin on the hands typically ages more quickly than any other skin location, due in part to the paucity of the subcutaneous fat layer that is important in providing cytokines and growth factors to dermal fibroblasts. Hand skin is also thinner than, for example, skin on the face.

The hands of a 59-year female were treated with 2.5 mL of HA-PE-2 mixed with a NIVEA Creme base cream, prepared according to Example 4, 203 times daily for 10 days. Prior to beginning the treatment period, the hand skin had small fibrotic scars or wrinkles and a dry/scaly appearance; following treatment, the hand skin was more luminescent, had lost the dry, scaly appearance, and the fibrotic scarring had dramatically reduced. Within 2 weeks of the cessation of treatment, the treated areas had reverted to a drier appearance but the small scars did not reappear.

Example 15. Treatment of Inflammation Associated with Actinic Keratosis

A subject previously treated for actinic keratosis lesions with liquid nitrogen was treated with a HA-PE-2 containing cream mixed with a NIVEA Creme base cream according to Example 4. Treatment consisted of the application of ~2.5 mL of the cream to one side of his scalp once daily for 7-10 days following treatment with nitrogen to remove the lesions. During the course of treatment inflammation was strongly reduced and the healing rate of the lesions was increased in the treated as compared to a skin cream provided by the dermatologist who had removed the lesions. This finding is consistent with evidence that native or high molecular weight hyaluronan has anti-inflammatory properties, which is one of the functions of naturally occurring hyaluronan within the skin.[6]

Example 16. Treatment of Dry Facial Skin

A 25 year old female prone to acne was placed on a systemic tretinoin A regimen. The treatment, together with daily swimming in chlorinated pools resulted in extremely dry and painful facial skin, in particular with cracked and flaky skin around the mouth. The subject was treated with HA-PE-2 mixed in an Oil of Olay™ base cream, prepared according to Example 4, for one week. At the end of the treatment period, the dry appearance and associated pain in the facial skin had disappeared. The treatment did not affect, positively or negatively, the underlying acne.

Example 17. Treatment of Scarred Skin

A professional musician with fibrotic scarring on his shoulder owing to years of playing the viola applied a cream containing HA-PE-2, prepared according to Example 4, by rubbing ~2.5 mL of the cream into the scarred skin once daily for 30 days. At the end of the treatment period the scarring, which had been present for years, had disappeared.

Example 18. Treatment of Cracked Skin on Fingers

Cracked skin on the fingers of a number of musicians (playing cello, violin, viola and piano) were treated with compositions containing HA-PE-2 prepared according to Example 4. In stringed instrument musicians, thumb skin in particular cracks during winter weather due to pressure against the frog of the bow while playing the instrument in dry, cold weather. In pianists, especially in older musicians, cracks often appear in the skin of fingers tips, likely owing in part to pressure exerted on the finger tips during practice.

Three stringed instrument musicians and two pianists applied a cream (~1 mL) prepared with HA-PE-2 and a NIVEA Creme base cream (prepared according to Example 4) to their cracked finger tips, resulting in the disappearance of cracked skin within 3-4 days. The use of other creams in the past, including the NIVEA Creme base cream used in Example 4, had no effect on the healing of the cracked skin.

Example 19. Treatment of Cracked Skin on Heals

With age, it is common for the skin on heels to become thick and prone to cracking, particularly during cold, dry winter months. Three individuals, aged 55-65 years, with severely cracked heels, causing pain while walking, applied ~2.5 mL of a cream containing HA-PE-2 prepared according to Example 4 with a NIVEA Creme base cream to their heels each evening for 5-7 days. Each individual noticed an improvement in their condition, including the ability to walk without pain, within 2-3 days. Following cessation of treatment, benefits of the treatment disappeared within 5-7 days. Re-application of the cream for 2-3 days again reduced the severity of the cracking and pain for each individual. Use of the base cream alone did not provide relief to any of the individuals.

Example 20. Treatment of Facial Skin

Three individuals applied a cream containing HA-PE-2 prepared according to Example 4 with a NIVEA Creme base cream to facial skin 1-2 times per day. Within 1 week of commencing treatment, an increase in skin luminosity and smoothness was observed. During this time the skin exhibited increased hydration (application was during winter months where colder temperature leads to drier skin) and small wrinkles around the eyes had disappeared. After 1 month of continued treatment, the initially observed effects were enhanced and skin had a thicker appearance, particularly around the eyes, and the appearance of wrinkles around the lips was reduced. Following termination of the treatment period, the treated areas reverted to their former state of dryness, with wrinkles around the eyes and lips gradually reappearing.

As many changes can be made to the embodiments described above without departing from the scope of the invention, it is intended that all material contained herein be interpreted as illustrative of the invention and not in a limiting sense.

The documents referenced within the preceding description are as follows:
HBdocs—10282653v1

[1] Fisher, G. J.; Varani, J.; Voorhees, J. J. *Archives of Dermatology.* 2008, 14495), 666-6672.

[2] Verdier-Sérvrain, S.; Bonté, F. *Journal of Cosmetic Dermatology* 2007, 6(2), 75-82.

[3] Baumann, L. *Journal of Pathology* 2007, 211(2), 241-251.

[4] Tammi, M. I.; Day, A. J.; Turley, E. A. *The Journal of Biological Chemistry* 2002, 277(7), 4581-4584.

[5] Kaya, G.; Tran, C.; Sorg, O.; Hotz, R.; Grand, D.; Carraux, P.; Didierjean, L.; Stamenkovic, I.; Saurat, J.-H. *PLoS Medicine* 2006, 3, e493 (2291-2303).

[6] Stern, R.; Maibach, H. I. *Clinics in Dermatology* 2008, 26, 106-122.

[7] Wiest, L.; Kerscher, M. *Journal der Deutschen Dermalologischen Gesellschaft (JDDG)* 2008, 6(3), 176-180.

[8] Masferrer, J. P.; Mejia, M. M.; Fernández, M. V.; Astudillo, A. A.; Armenteros; A. L. H.; Hernández, V. M.; Perez, R. S.; Ferre, A. M. *Clinical & Translational Oncology.* 2010, 12, 43-48.

[9] Tzellos, T. G.; Klagas, I.; Vahtsevanos, K.; Triaridis, S.; Printza, A.; Kyrgidis, A.; Karakiulakis, G.; Zouboulis, C. C.; Papakonstantinou, E. *Experimental Dermatology* 2009, 18, 1028-1035.

[10] Yu, Q.; Banerjee, S. D.; Toole, B. P. *Developmental. Dynamics.* 1992, 193(2), 145-151.

[11] Rilla, K.; Tolhonen, R.; Kultti, A.; Tammi, M.; Tammi, R. *Journal of Histochemistry & Cytochemistry* 2008, 56(10), 901-910.

[12] Buchanan, E. P.; Longaker, M. T.; Lorenz, H. P. *Advances in Clinical Chemistry* 2009, 48, 137-161.

[13] Webber, J.; Meran, S.; Steadman, R.; Phillips, A. *The Journal of Biological Chemistry* 2009, 284(14), 9083-9092.

[14] Brown, T. J.; Alcorn, D.; Fraser, J. R. E. *The Journal of Investigative Dermatology* 1999, 113, 740-76.

[15] Zhang, L.-S.; Greyner, H. J.; Mummert, M. E. *Journal of Dermatological Science* 2009, 55, 56-59.

[16] Ionzzo, M.; De Padova, M. P.; Tosti, A. *Clinics in Dermatology* 2008, 26, 177-181.

[17] Antosova, A.; Mackova, M.; Kral, V.; Macek, T. *Trends in Biotechnology* 2009, 27, 628-635.

[18] Gebhardt, C.; Averbeck, M.; Diedenhofen, N.; Willenberg, A.; Anderegg, U.; Sleeman, J. P.; Simon, J. C. *Journal of Investigative Dermatology* 2010, 130, 141-149.

[19] Tolg, C.; Poon, R.; Foode. E.; Turley, E. A.; Alman, B. A. *Oncogene* 2003, 22, 6873-6882.

[20] Tolg, C.; Hamilton, S. R.; Nakrieko, K.-A.; Kooshesh, F.; Walton, P.; McCarthy, J. B.; Bissell, M. J.; Turley, E. A. *Journal of Cell Biology* 2006, 175(6), 1017-1028.

[21] Koepke, J. I.; Nakrieko, K.-A.; Wood, C. S.; Boucher, K. K.; Terlecky, L. J.; Walton, P. A.; Terlecky, S. R. *Traffic* 2007, 8, 1590-1600.

[22] Tolg, C.; Hamilton, S. R.; Nakrieko, K.-A.; Kooshesh, F.; Wlaton, P.; McCarthy, J. B.; Bissell, M. J.; Turley, E. A. *Journal of Cell Biology* 2006, 175(6), 1017-1028.

[23] Girish, K. S.; Kemparaju, K.; Nagaraju, S.; Vishwanath, B. S. *Current Medicinal Chemistry* 2009, 16, 2261-2288.

[24] Sugino, M.; Todo, H.; Sugibayashi, K. *Yakugaku Zasshi* 2009, 129(12), 1453-1458 (abstract).

[25] Skountzou, I.; Kang, S.-M. *Current Topics in Microbiology and Immunology* 2009, 333, 347-368.

The embodiments of the invention in which an exclusive property or privilege is claimed are as follows:

1. A non-particulate glycosaminoglycan composition comprising a glycosaminoglycan modified through the covalent linkage of a lipid moiety to about 1-15% of the repeating disaccharide monomer units of the glycosaminoglycan wherein:
   the glycosaminoglycan to be modified is hyaluronan, a hyaluronan derivative, a polysaccharide comprised of repeating disaccharide units of an uronic acid or hexose linked to a hexosamine, or derivatives thereof;
   the glycosaminoglycan moiety in the composition having a molecular weight in the range of about 50 kDa to about 2,500 kDa;
   the lipid moiety comprises one or more naturally-occurring or synthetically-derived fatty acids, glycerolipids, phospholipids, sphingolipids, sterol lipids, prenol lipids, or derivatives thereof, provided that the lipid moiety contains a functional group on its polar head-group to allow for covalent linkage of the lipid to the glycosaminoglycan.

2. The glycosaminoglycan composition of claim 1, wherein the glycosaminoglycan is modified through the covalent linkage of a lipid moiety to 5.5% or 6% of the repeating disaccharide monomer units of the glycosaminoglycan.

3. The glycosaminoglycan composition of claim 1, wherein the glycosaminoglycan is modified through the covalent linkage of a lipid moiety to a range between 2.6% and 7.5% of the repeating disaccharide monomer units of the glycosaminoglycan.

4. The glycosaminoglycan composition of claim 1, wherein the glycosaminoglycan moiety has a molecular weight in the range of about 100 kDa to about 2,000 kDa.

5. The glycosaminoglycan composition of claim 1, wherein the glycosaminoglycan moiety has a molecular weight in the range of about 350 kDa to about 1,500 kDa.

6. The glycosaminoglycan composition of claim 1, wherein the glycosaminoglycan moiety has a molecular weight in the range of about 500 kDa to about 1,500 kDa.

7. The glycosaminoglycan composition of claim 1, wherein the glycosaminoglycan to be modified is hyaluronan or a hyaluronan derivative.

8. The glycosaminoglycan composition of claim 7, wherein the glycosaminoglycan to be modified is hyaluronan.

9. The glycosaminoglycan composition of claim 1, wherein the lipid moiety contains an amino group on its polar head-group and is covalently bound to the glycosaminoglycan via an amide linkage to a carboxylic acid group on the glycosaminoglycan.

10. The glycosaminoglycan composition of claim 1, wherein the lipid moiety comprises one or more phosphatidylethanolamines or phosphatidylserines.

11. The glycosaminoglycan composition of claim 1, wherein the lipid moiety comprises one or more phosphatidylethanolamines.

12. A The glycosaminoglycan composition of claim 1 in admixture with one or more cosmetically or pharmaceutically acceptable excipients or carriers.

13. The composition of claim 12, wherein the glycosaminoglycan is modified through the covalent linkage of a lipid moiety to 5.5% or 6% of the repeating disaccharide monomer units of the glycosaminoglycan.

14. The composition of claim 12, wherein the glycosaminoglycan is modified through the covalent linkage of a lipid moiety to a range between 2.6% and 7.5% of the repeating disaccharide monomer units of the glycosaminoglycan.

15. The composition of claim 12, wherein the glycosaminoglycan moiety has a molecular weight in the range of about 100 kDa to about 2,000 kDa.

16. The composition of claim 12, wherein the glycosaminoglycan moiety has a molecular weight in the range of about 350 kDa to about 1,500 kDa.

17. The composition of claim 12, wherein the glycosaminoglycan moiety has a molecular weight in the range of about 500 kDa to about 1,500 kDa.

18. The composition of claim 12, wherein the glycosaminoglycan is hyaluronan.

19. The composition of claim 12, wherein the lipid moiety contains an amino group on its polar head-group and is covalently bound to the glycosaminoglycan via an amide linkage to a carboxylic acid group on the glycosaminoglycan.

20. The composition of claim 12, wherein the lipid moiety comprises one or more phosphatidylethanolamines or phosphatidylserines.

21. The composition of claim 12, wherein the lipid moiety comprises phosphatidylethanolamines.

22. The composition of claim 12, additionally comprising one or more ingredients that are transported across the epithelium by the glycosaminoglycan.

23. The composition of claim 22, wherein the additional one or more ingredients comprises anti-oxidants, vitamins, essential oils, UV-blocking agents, or other nutrients whose application is known to provide a beneficial effect to the health or appearance of skin.

24. The composition of claim 22, wherein the additional one or more ingredients is a pharmaceutical.

25. The composition of claim 24, wherein the additional one or more ingredients comprises therapeutic agents suitable for the treatment of inflammation, skin cancer or skin conditions that are delivered through the epithelium.

26. The composition of claim 25, wherein the additional one or more ingredients is suitable for the treatment of skin cancer.

27. The composition of claim 25, wherein the additional one or more ingredients is suitable for the treatment of skin conditions.

28. The composition of claim 24, wherein the additional one or more ingredients comprises an anti-inflammatory agent.

29. The composition of claim 24, wherein the additional one or more ingredients comprises a prostaglandin.

30. The composition of claim 22, wherein the additional one or more ingredients comprises a protein, peptide, peptide mimetic, pepducin, polynucleotide, or other biomolecule.

31. The composition of claim 30, wherein the additional one or more ingredients has a molecular weight of between about 700 Da and about 500 kDa.

32. The composition of claim 30, wherein the additional one or more ingredients comprises collagen that is delivered across the epithelium.

33. The composition of claim 31, wherein the additional one or more ingredients comprises a protein.

34. The composition of claim 33, wherein the protein is a botulinum toxin that is delivered across the epithelium.

35. The composition of claim 34, wherein the protein is botulinum toxin type A.

36. The composition of claim 33, wherein hyaluronan synthase is delivered across the epithelium.

37. The composition of claim 31, wherein the additional one or more ingredients comprises a pepducin, a hyaluronidase inhibitor or a RHMM inhibitor.

38. A method for the manufacture of a glycosaminoglycan composition of claim 1 comprising the steps of:
   treating the, having a molecular weight in the range of about 50 kDa to about 2,500 kDa, with an activating agent to facilitate covalent bonding of the glycosaminoglycan to the lipid moiety;
   reacting the activated glycosaminoglycan and lipid moiety; and
   allowing the lipid moiety to react with the activated glycosaminoglycan to covalently link the lipid moiety to the glycosaminoglycan,
   wherein the activating agent is the limiting reagent in the reaction, the lipid moiety in the reaction being in molar excess of the amount of activating agent used and the activating agent being added in an amount sufficient to facilitate covalent linkage of the lipid moiety to about 1 to about 15% of the disaccharide monomer units of the glycosaminoglycan.

39. The method according to claim 38 wherein the activating agent is a carbodiimide.

* * * * *